United States Patent [19]

Chareire

[11] Patent Number: 4,872,665
[45] Date of Patent: Oct. 10, 1989

[54] MECHANICAL LEG-PROPULSION ASSISTANCE DEVICE

[76] Inventor: Jean-Louis Chareire, 66, rue Artistide Briand, 92300 Levallois Perret, France

[21] Appl. No.: 920,072

[22] Filed: Oct. 16, 1986

[30] Foreign Application Priority Data

Oct. 30, 1985 [FR] France ................. 85 16097

[51] Int. Cl.$^4$ ............................................ A63B 29/00
[52] U.S. Cl. ..................................... 272/70; 128/25 R
[58] Field of Search ....................... 272/70, 70.3, 70.4; 128/25 R, 25 B, 80 G; 623/26, 27

[56] References Cited

U.S. PATENT DOCUMENTS

| 406,328 | 7/1889 | Yagn | 272/70 |
| 440,684 | 11/1890 | Yagn | 272/70 |
| 2,111,018 | 3/1938 | Ahler | 623/26 |
| 2,210,269 | 8/1940 | Taylor | 272/70 |
| 3,529,474 | 9/1970 | Olson et al. | 272/70 X |
| 3,683,897 | 8/1972 | Shield et al. | 128/25 R |
| 3,976,057 | 8/1976 | Barclay | 128/25 R |
| 4,557,257 | 12/1985 | Fernandez | 128/80 G |
| 4,651,719 | 3/1987 | Funk et al. | 128/25 R |

FOREIGN PATENT DOCUMENTS

| 247482 | 5/1912 | Fed. Rep. of Germany | 272/70 |
| 846891 | 8/1952 | Fed. Rep. of Germany | |
| 3227359 | 2/1983 | Fed. Rep. of Germany | |
| 593056 | 11/1977 | Switzerland | 128/80 G |

Primary Examiner—Richard J. Apley
Assistant Examiner—H. Flaxman
Attorney, Agent, or Firm—Roland Plottel; Richard S. Roberts

[57] ABSTRACT

A leg-propulsion assistance device for improving the individual field of a mobility of a human being. The device provides a saddle supplied with a hip fastening device. A saddle joint allows for the swiveling movement of two telescopic rods, the extension force of which is derived from a compressed spring or fluid generated under pressure, by a motor-compressor set. A link arm transmits the movement to a fixed joint in front of the user's shoe. A joint which becomes freed automatically at the end of each propulsive stride allows the link arm and foot to be raised. An automatic piloting system synchronizes the motive force with the muscular extension force of the leg and foot. The invention relates to all applications necessitating propulsion by the legs of an individual capable or not capable of exerting an intense muscular effort.

10 Claims, 12 Drawing Sheets

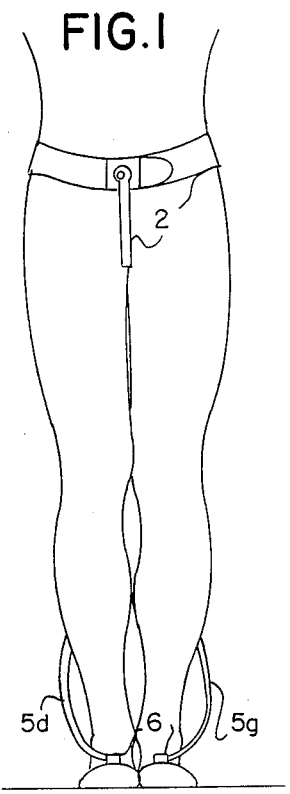
FIG. 1
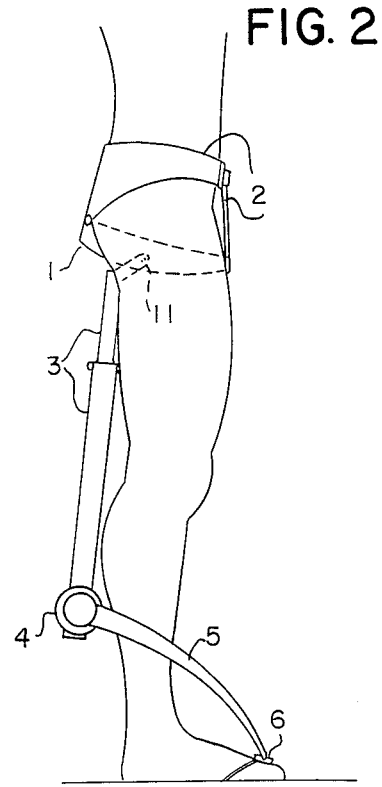
FIG. 2
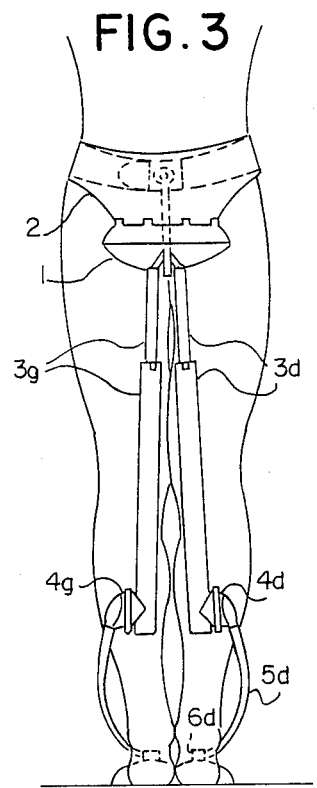
FIG. 3
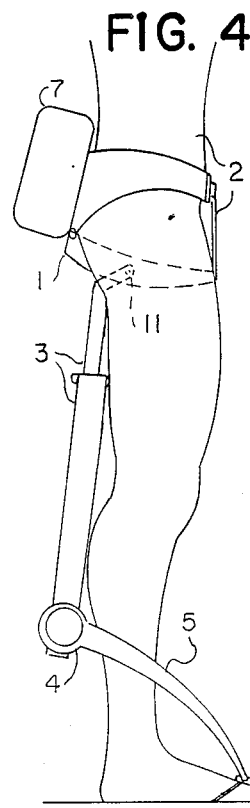
FIG. 4
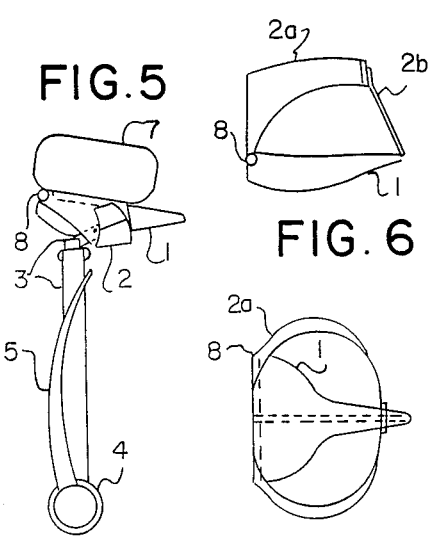
FIG. 5
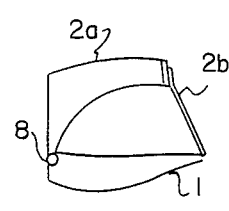
FIG. 6
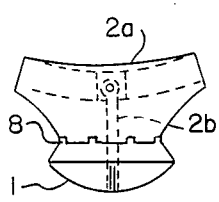
FIG. 7
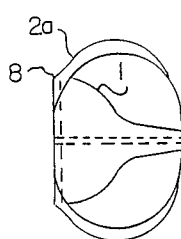
FIG. 8
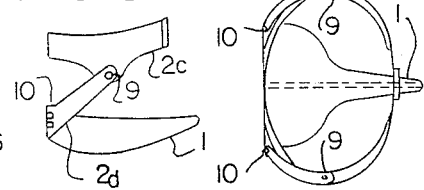
FIG. 9
FIG. 10
FIG. 11
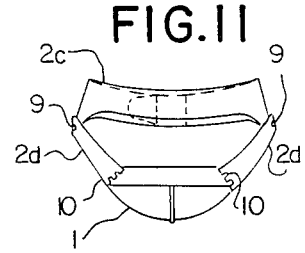

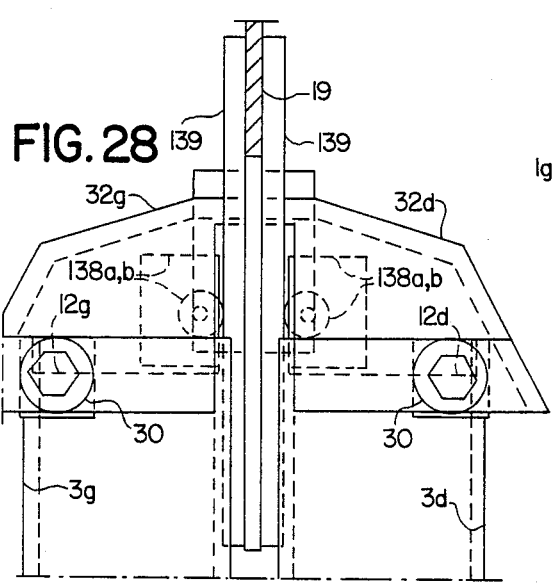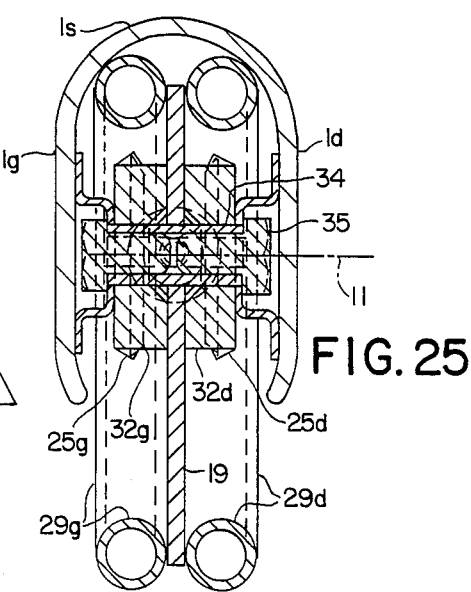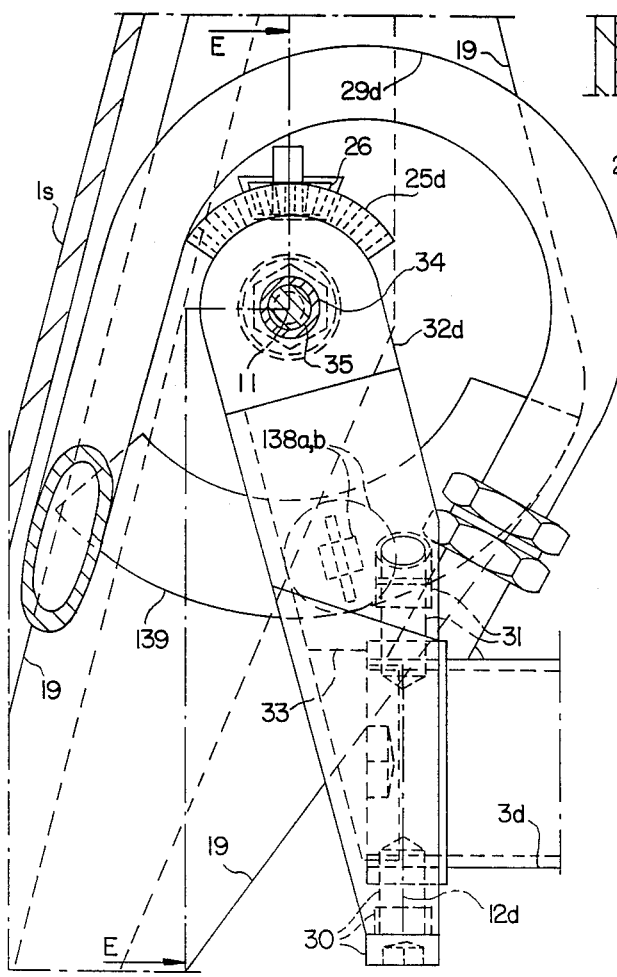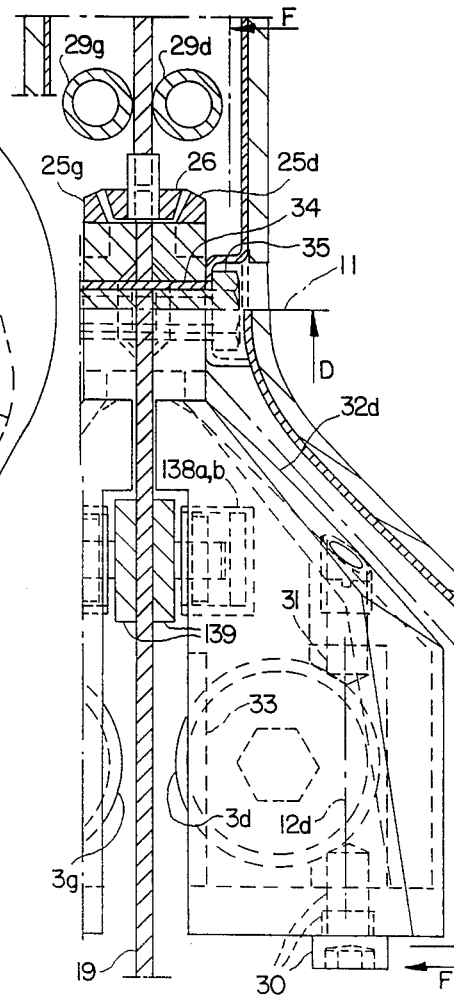

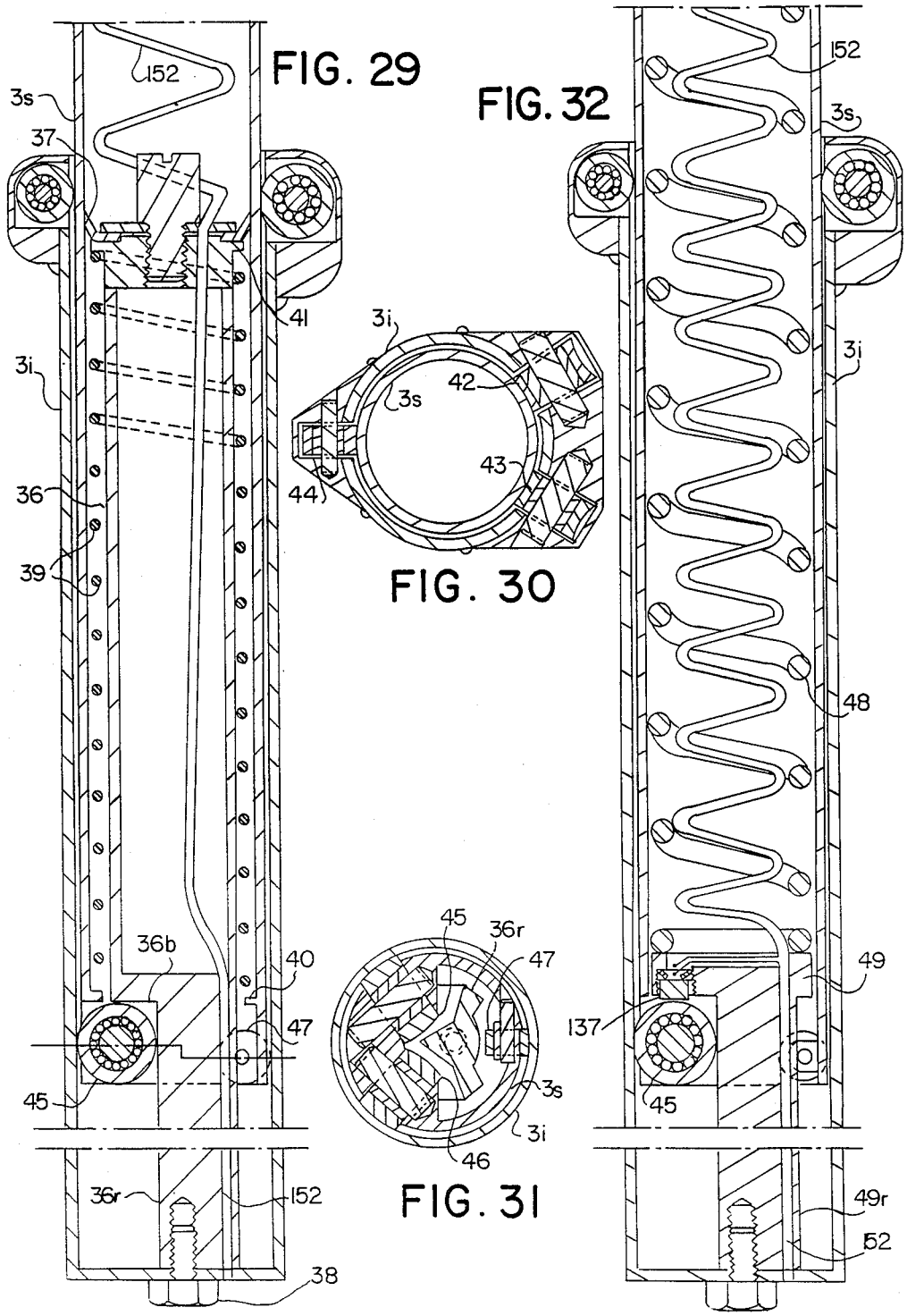

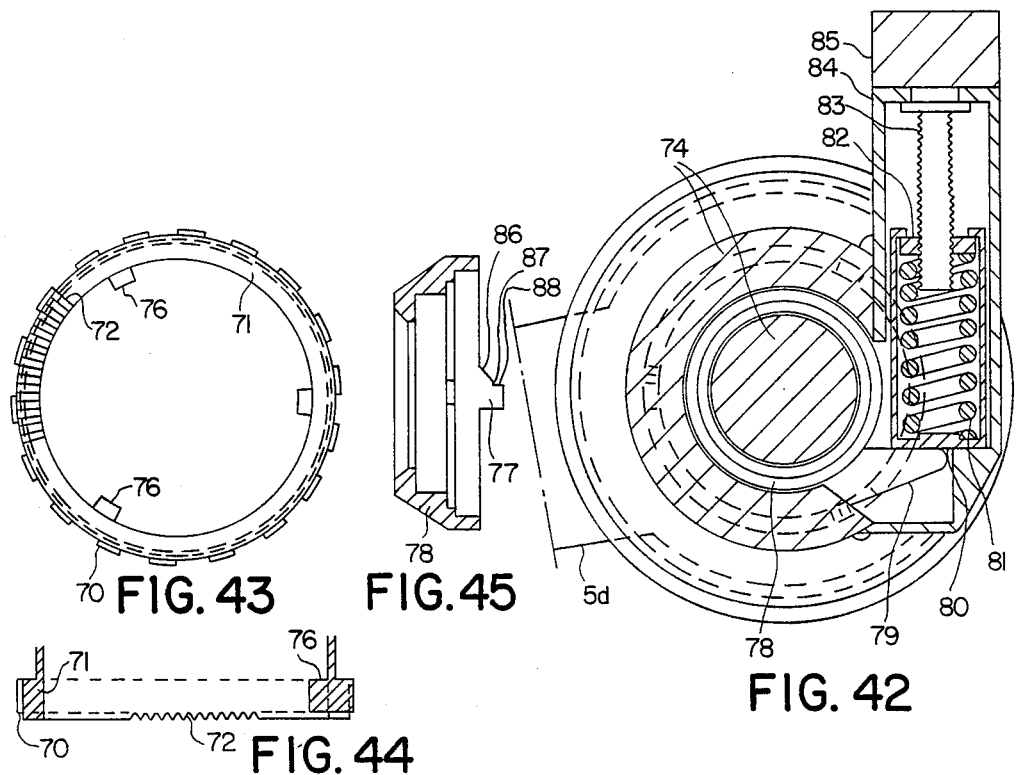
FIG. 43  FIG. 45  FIG. 42
FIG. 44
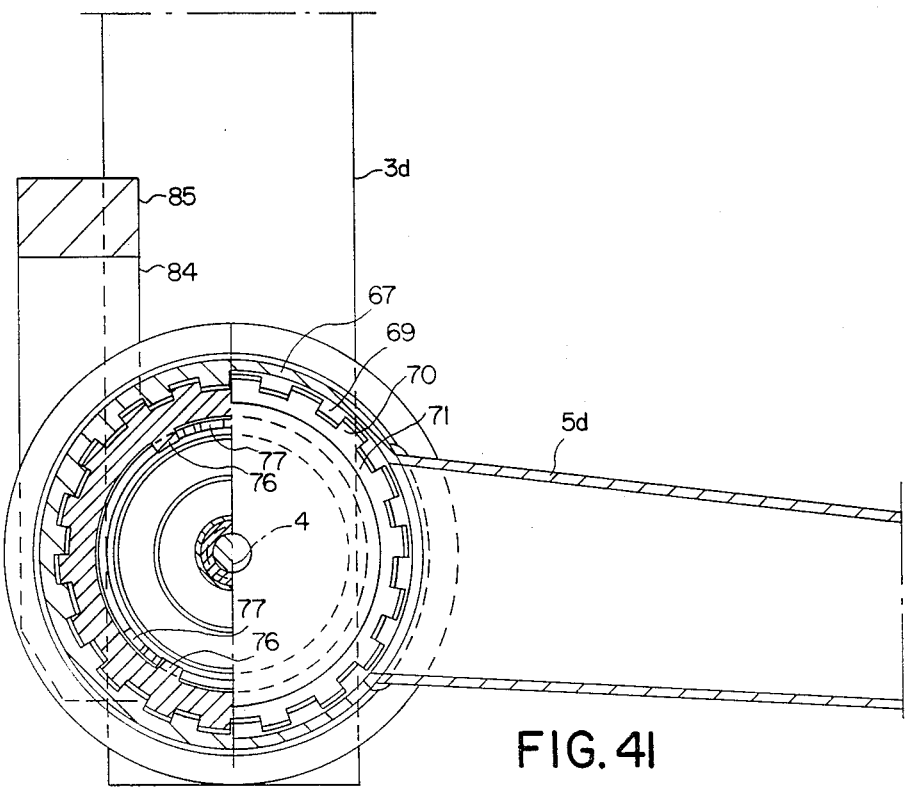
FIG. 41

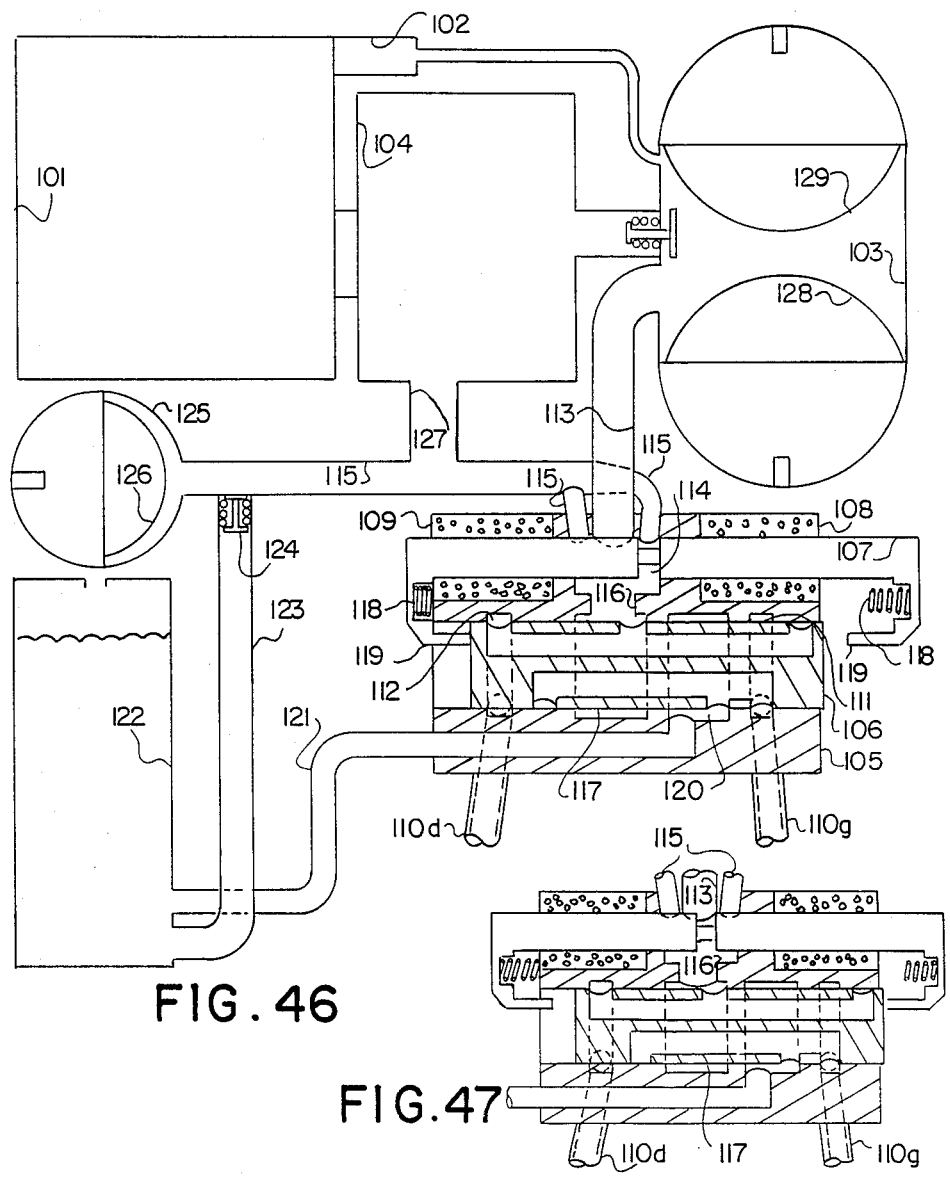
FIG. 46
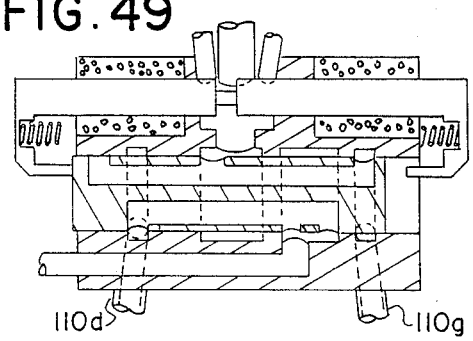
FIG. 49
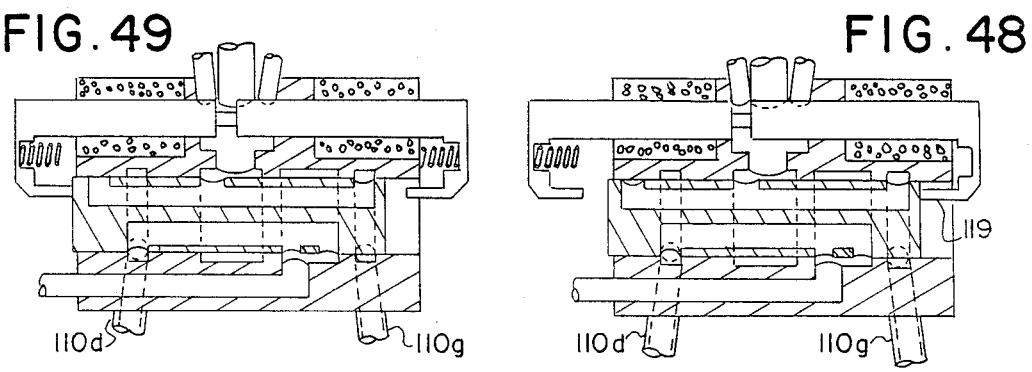
FIG. 47
FIG. 48

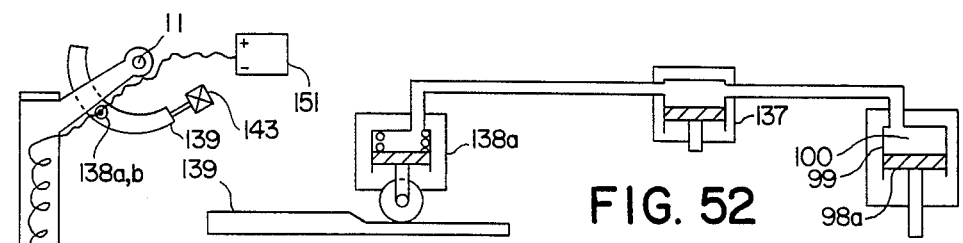
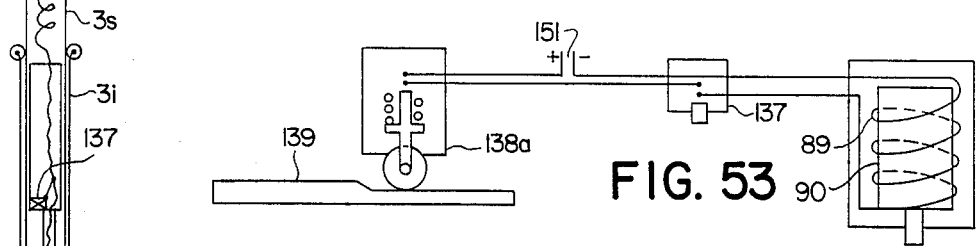
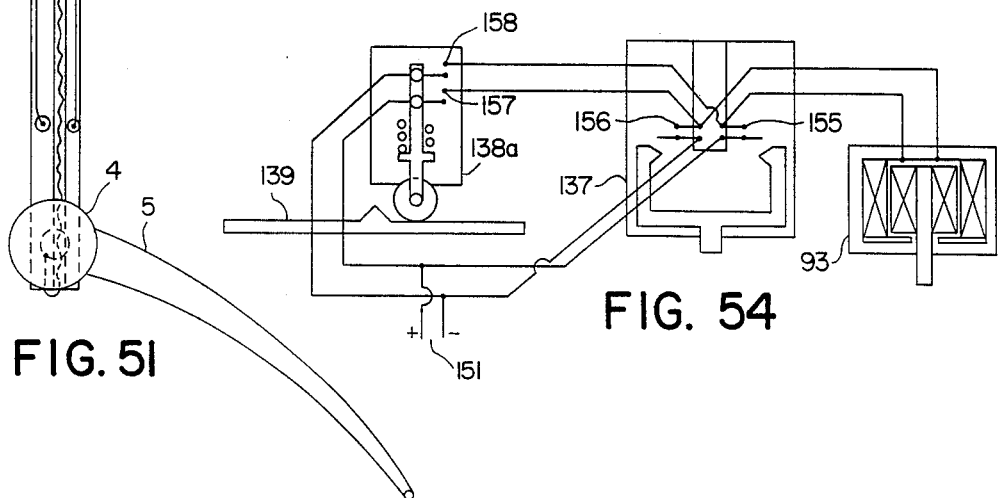
FIG. 51
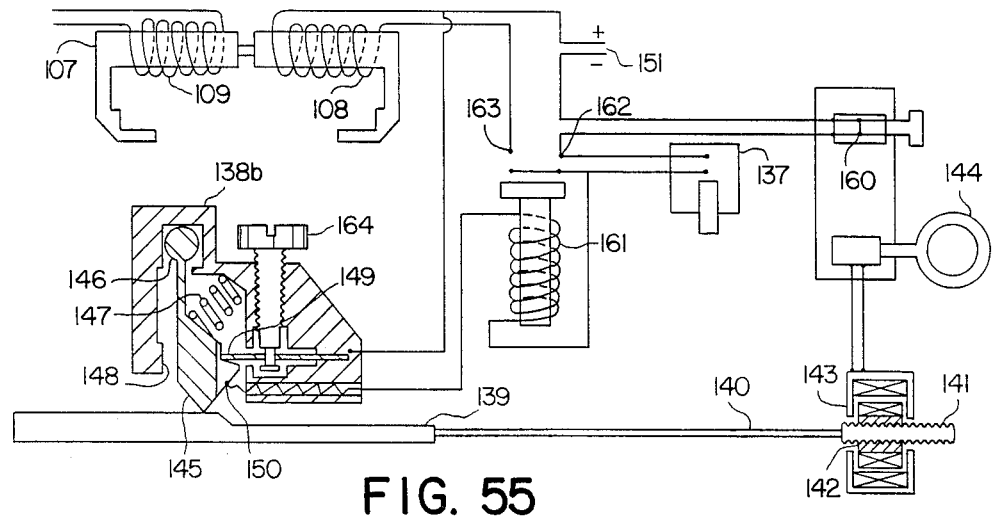

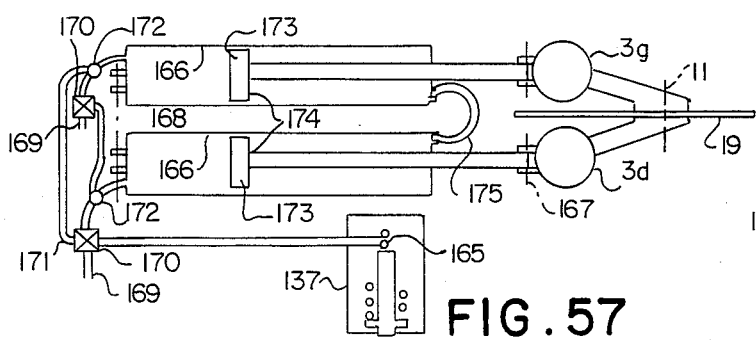
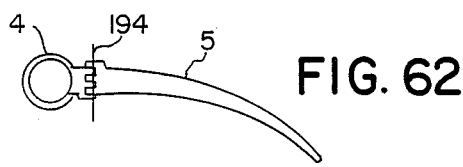
FIG. 57
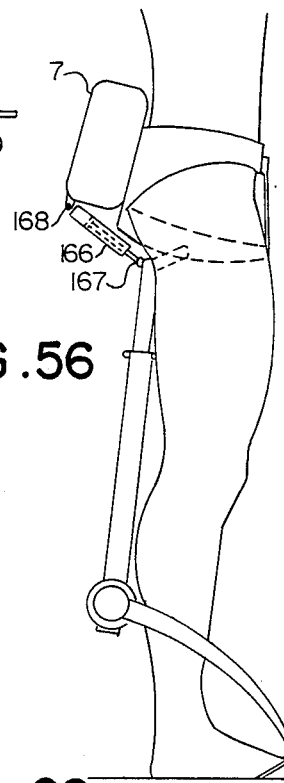
FIG. 56
FIG. 62
FIG. 58　FIG. 59　FIG. 60　FIG. 61
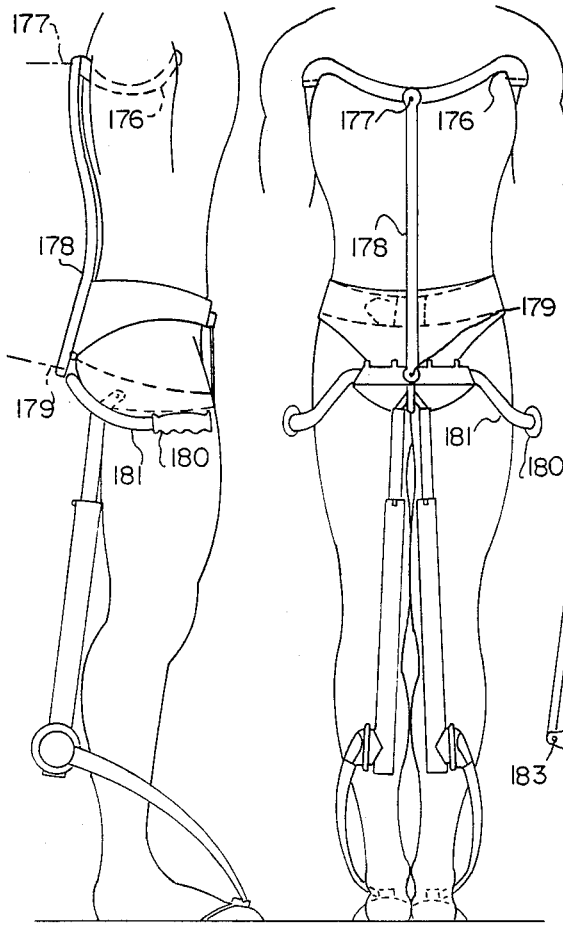
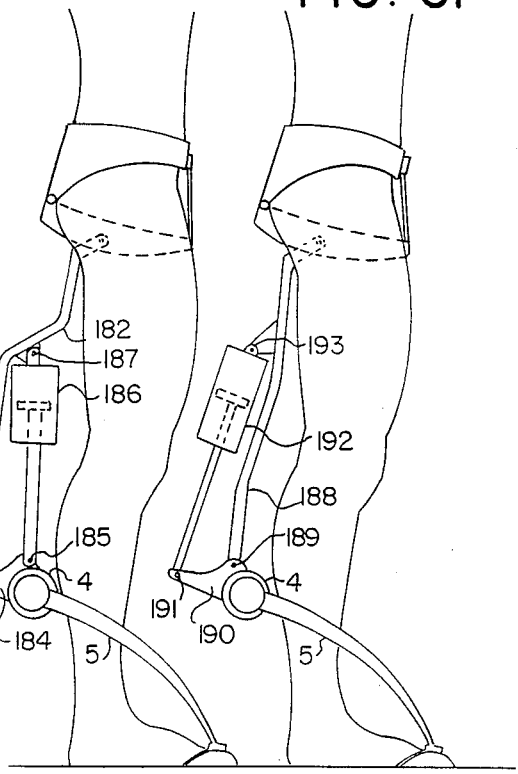

MECHANICAL LEG-PROPULSION ASSISTANCE DEVICE

BACKGROUND OF THE INVENTION

The present invention concerns the field of individual mobility of a human being and more particularly mechanical assistance in leg propulsion Propulsion by means of the legs, which calls upon the muscles situated in the pelvis and legs, conditions in particular all non-motorized land movements by man and includes such activities as: Walking, running, jumping and going up or down a slope.

This propulsion by means of the legs als allows certain accessory devices to be used which favor movement over various land or water surfaces and includes, for example:

Skis, ice skates, roller skates, bicycles and various land or sea engines propelled by pedalling or similar means.

Finally, the muscles used in leg-propulsion also enable an individual to remain in a static bending position as regards the lower parts of his body in order to, for example, carry out certain tasks. The aim of the invention, which concerns a mechanical leg-propulsion assistance device, is to increase the individual's natural performances as regards all the previously cited uses. The device acts in such a way as to reinforce the natural propulsive system of a man, whilst enabling him to use the force accrued in a wide variety of ways. The researches carried out to determine the state of the possible previous art have revealed the following two categories of inventions:

Firstly, raised shoes with springs under the sole or with spring stilts. Secondly, a certain number of prostheses for the lower limbs and designed to act as a skeleton or, exceptionally, designed to enable paraplegics to walk slowly.

The shoes or spring stilts are radically different from the present invention in that firstly they merely amplify a natural movement and not its parallel mechanical assistance. Indeed, the increase in force which they produce is transmitted solely to the body by the skeleton of the legs Secondly, these shoes or spring stilts which lift in particular the foot disturb the natural equilibrium. The prostheses seeking to replace the skeleton lacking a lower limb do not aid propulsion. Finally, the prostheses designed to enable paraplegics to walk have a geometry inspired by that of the skeleton and which in particular includes the knee joint. This disposition, totally different to that of the device according to the invention, scarcely favors the exercising of very strenuous forces required to propel the individual vertically and results in a device which is heavy and clumbersome.

The shape of the device according to the invention is, conversely, designed so that ascending forces can quickly be exerted on the body, but it applies to normal or physically small individuals who are able to move their feet during a movement and exercise their natural equilibrium.

Moreover, with the foot resting on the ground and the device not impeding any natural movement, the conditions governing the individual's equilibrium are not disturbed. In addition, the device allows for the cumulative use of such accessories as skis, skates, etc., without the natural equilibrium, which learns to adapt itself to each of these uses, being in any way modified.

The invention's spheres of application are numerous and, without such list being in any way restrictive, include the following examples All movements of a sportive, utility or tourist nature made by individuals having a normal musculature.

Without additional accessories, movements on rocky, sandy, marshy or very steep mountainous terrains not suitable for motor vehicles, stairs and all places where it is necessary to negotiate obstacles and climb long and steep slopes.

With skis supplied for temporary hillside use with a coating prohibiting slipping backwards, such as seal skins, the possibility of climbing the steepest slopes without fatigue. With ice skates, frozen smooth stretches can be traversed quickly. With a bicycle without its original saddle or another land-based engine propelled by pedalling or similar means or roller skates having a sufficient diameter, movements over roads of average distance can be effected. The existence of light detachable accessories thus enables a movement to be effected over a very open-ended distance, accessible or not accessible to roads. Finally, it is possible to carry out nautical movements with a propeller or paddle boat, the energy of which is distributed over a crank gear or similar mechanism.

Individual movements of physically handicapped persons:

Assistance in moving for persons with very weak muscles with the possibility of access to the previous headings.

Aid for the partially disabled, such as individuals suffering from serious affections of the cardiovascular system or the after-effects of poliomyelitis for example, enabling them to ascend or go down steep slopes inaccessible to wheelchairs or stairs. Possible assistance to the spine through additional support to the shoulders and the possibility of partial support by the hands. Standing position assistance.

Assistance in working:

Assistance in climbing or descending slopes not accessible to motor vehicles or stairs in the construction industry and civil engineering works in certain mines, etc.

Carriage on a man's back of heavy loads over diverse terrains.

Towing by a man of loads and tools on terrain not suitable for motor vehicles.

Static bending support of the legs for painters, mechanics, etc.

Athletics:

The use of this device for leaping movements or rapid climbing gives its users a sensation which combines the sensation they might feel on the saddle of a moving horse or on a motocross saddle.

All these applications are thus likely to improve the quality of life of a large number of individuals and represent an important industrial opportunity.

SUMMARY OF THE INVENTION

These objectives are attained with the system according to the invention, thanks to the following means:

The device is provided with a saddle where the ascending thrust forces converge and are transmitted to the body. This saddle, which for the majority of usages is not continuously subjected to ascending forces, comprises a device to be secured to the hips of the individual and closed by a belt buckle which enables him to always exert a certain minimum support force under the bottocks so as to retain firm contact at all times. In certain cases, the hip fastener can be replaced or supplemented by a fastener over the shoulders. A joint whose axis is roughly perpendicular to the center plane of the body is fixed under the saddle and two telescopic devices are connected to it symetrically in relation to the center plane so that they can each perform a pendulum movement under the saddle around this axis.

The shape of the telescopic devices and the location of the joint under the saddle enable them to carry out their pendulum movements in tune with those of the legs without colliding with the outer spatial requirements of the back and inside of the legs.

The disposition at the back of the legs of the individual is in effect less bulky and more readily compatible with natural movements. The telescopic devices moreover include close to their joint on the saddle a supplementary joint whose axis is roughly parallel to the center plane of the body, this added joint allowing for any lateral spreading of the legs.

The joints whose axis is roughly perpendicular or parallel to the center plane and which are situated in the saddle zone and connected to the telescopic devices are preferably placed in this order, extending from the saddle towards the telescopic devices, but the reverse order is possible with the present invention. The terms "roughly parallel" or "roughly perpendicular" are used to define a certain number of directions characteristic of the invention, such as the directions actually selected for technological commodities which may deviate by up to 15° or 20° for example from the pure parallel or perpendicular direction, but without resulting in a modification of the basic function of the joint in question.

The functions required to be fulfilled by the telescopic devices are firstly, the exertion of a force when they are extended and secondly, resisting the torque which results from the fact that the force is not exerted within the axis of the telescope but is applied to the extremity of the link arm with the foot. The telescopic device may therefore comprise a rectilinear or curved male part and rectilinear or curved female part sliding into each other, this sliding being effected by means of a small wheel or ball system or any other process possibly comprising an intermediate cage capable of avoiding jamming at the time of sliding under the effect of the torque. In another version of the invention, the telescopic device may include, instead of the small wheels mentioned above, a rigid bar and three supplementary joints, all of which free the telescope from the effects of the torque at the cost of a larger spatial requirement. Around the saddle joint whose axis is roughly perpendicular to the center plane, it is possible to place a set of three bevel gear pairs, two of which are integral with the pendulum movements of the telescopic devices and the axis of the third is inside the center plane and secured to the saddle, which angularly stabilizes the latter in relation to the bisectrix of the legs.

From the saddle, the telescopic devices descend towards the ground, preferably remaining some distance from each other with the legs being kept close together so that the devices remain entirely or almost entirely at the back of the legs and as close as possible to them without impeding them.

The lower extremity of the telescopic devices, that is the one opposite the joints under the saddle, is connected by a joint, whose axis is roughly perpendicualr to the center plane of the body, to a link arm where another joint, roughly parallel to the previous one, connects the front part of the shoe. The shape of the arm is such that it enables it to carry out significant angular movements around its two joints, preferably without impeding the shoe, ankle or lower part of the calf.

The joint which connects the link arm to the base of the telescopic device is supplied with a ratchet which authorizes the individual lowering of the foot and link arm until the movement of the latter stops, but which prohibits, upon the foot being lifted up again, the raising of the link arm independently of the lifting of the telescopic device in question. This ratchet may be put out of service by an electrical or hydraulic device upon the order of an electrical or hydraulic signal generated by the arrival at the maximum extension position of the telescopic device solely when this maximum extension occurs as regards a foot position behind the body, that is at the end of the propulsion phase. Thus, at the end of this phase, the foot can be lifted up again which enables it to again pass in front of the other foot which is on the ground without impeding the ground. The distance, measured when the individual is standing erect, between the base of the telescopic device and a level piece of ground, is preferably sufficient to avoid any direct impact with the ground during certain phases of the act of movement or leaping or when descending slopes, stairs, etc.

The telescopic device is fitted with internal means, pistons, cylinders, etc., which enable it to exert considerable force when extended under the effect of a previous compressed or the pressure of a fluid. If the lower joint of the telescopic device is blocked by its ratchet, this force is transmitted firstly to the extremity of the link arm and thus to the front part of the shoe, and secondly, to the saddle via its joint.

The exertion of this force is synchronized with all the muscular efforts extending the leg and foot, either naturally if the force is due to the spring-back of a compressed spring in the front part of the stride, or by a piloting system based on the measurement of an angular position of the telescopic devices as regards authorization, and upon detection of their maximum extension as regards evacuation, if the force is due to a fluid pressure originating from a generator. The fluid under pressure generator is generally a motor-compressor set which can be carried by the individual or consists of other autonomous means of generation, but it could also be a portable tank or flexible tube connected to a fixed compressed air source for short power range uses.

In addition to the preceding devices, the invention may be equipped with a mechanical system for aiding the pendulum movement of the legs. For this system, a point close to the top of each telescopic device is connected to a telescopic jack which takes support behind the saddle on a joint sufficiently rigidly linked to the latter. The telescopic jack is generally supplied by a compressed fluid simultaneously with the telescopic device to which it is not mechanically connected.

The device may include other points of support on the body other than the saddle. Indeed, it may have parallel lateral handles connected to the rear of the saddle, which, when an individual has the arms stretched alongside the body, enables him to receive a sizeable ascending vertical effort in the arms These handles also dispense with the need to secure the device to the body in certain cases, the device then being kept in position by the arms.

There may also exist a device for transmiting the ascending force received by the saddle as far as the shoulders thanks to a system of force transmission and support parts under the arms connected by possibly blockable joints.

Thus, in its essential elements, the innovation concerns a mechanical leg-propulsion assistance device to be applied, without changing an individual's conditions of equilibrium, in walking, running, jumping, going up and down slopes and in retaining a static leg bending position, the individual who is supplied with it also being able to be equipped with accessories favoring mobility, accessories such as skis, ice skates or roller skates, bicycles and various land-based or nautical engines propelled by pedalling or similar means, characterized in that:

It comprises a saddle generally supplied with means which enable it to be at least fastened to the hips and comprising at least one joint to which are connected the upper extremities of the two telescopic devices, symetrical in relation to the said center plane, descending towards the ground whilst respecting a sufficient distance and remaining preferably constantly behind and as close as possible to the legs, without hindering their movements. Close to the lower extremity of each telescopic device, a joint is fixed fitted with a blocking device capable of being put out of service or action towards the end of the propulsive stride made by the individual and generally for at least the time it takes to raise the foot in question again. This joint is connected to a link arm, whilst another joint connects the front part of the shoe or an accessory secured to the shoe. The shape of the said link arm enables it to carry out sufficient angular movements around its two joints, preferably without impeding the shoe, ankle or base of the calf. The telescopic devices are provided with means for exerting, simultaneously with the muscular extension effort of the leg and foot, a force due to a compressed spring or the pressure of a fluid which, when their lower joint is blocked, tends to move the joint of the saddle away from that of the shoe in question, which causes mechanical assistance to be given to the muscular effort.

BRIEF DESCRIPTION OF THE DRAWINGS

The invention will be more clearly understood from the detailed description of examples of embodiments and supported by the figures in the appendix and which represent the following:

FIG. 1: front view of a man equipped with the device according to the invention.

FIG. 2: side-face view of a man equipped with the device.

FIG. 3: view of the back of a man equipped with the device.

FIG. 4: side-face view of a man equipped with the device and showing a possible location for a fluid under pressure generator.

FIG. 5: side-face view of the device according to the invention, alone and in the filled state for transport or storage.

FIG. 6: side-face view of a saddle fitted with a first type of hip fastening device.

FIG. 7: Back view of this saddle and its fastening device.

FIG. 8: Top view of this saddle and its fastening device.

FIG. 9: side view of a saddle equipped with a second type of hip fastening device.

FIG. 10: Top view of this same saddle.

FIG. 11: Back view of this same saddle and its fastening device.

FIG. 25: Section along D of the central part of the saddle seen from the rear and showing a second mode of embodiment of the upper joints of the telescopic devices.

FIG. 26: Section along F—F showing the profile saddle with the second mode of embodiment of the upper joints of the telescopic devices.

FIG. 27: Section along E—E showing the saddle seen from above with the second mode of embodiment of the upper joints of the telescopic devices.

FIG. 28: View from the rear of the saddle of the top of the two telescopic devices showing the stop system established on one of the upper joints of the latter in the case of a second mode of embodiment.

FIG. 29: Profile cross section of a first telescopic device.

FIG. 30: Top cross section along its longitudinal axis of the first telescopic device showing the upper castors.

FIG. 31: Top cross section of the first telescopic device showing the lower castors.

FIG. 32: Profile cross section of a second telescopic device.

FIG. 41: Lateral cutaway view G—G of a blockable joint.

FIG. 42: Lateral cutaway view H—H of a blockable joint.

FIG. 43: Lateral view of the cylindrical blocking ratchet of the lower joint of the telescopic device.

FIG. 44: Cutaway view of the cylindrical ratchet.

FIG. 45: Lateral cutaway view of the part transmitting forces to the stop.

FIG. 46: Overall diagrammatic view of a liquid under pressure generator including the engine, compressor, tanks and slide valves of the telescopic device main pistons.

FIG. 47: Diagrammatic cutaway view of the slide valves of FIG. 46 in a 2nd position.

FIG. 48: Diagrammatic cutaway view of the slide valves of FIG. 46 in a 3rd position.

FIG. 49: Diagrammatic cutaway view of the slide valves of FIG. 46 in a 4th position.

FIG. 51: Diagrammatic overall profile view of the device according to the invention, excluding the saddle, showing the location of the blockable joint control devices.

FIG. 52: Skeleton diagram of the blockable joint hydraulic unblocking system.

FIG. 53: Skeleton diagram of a first electrical system for unblocking, by solenoid, the blockable joint.

FIG. 54: Skeleton diagram of a second system for unblocking, by engine and screw, the blockable joint.

FIG. 55: Skeleton diagram of one half of the feed-/evacuation control circuit of the telescopic devices.

FIG. 56: Outer profile view of the device according to the invention equipped with jacks for assisting the pendulum movement of the legs.

FIG. 57: Skeleton diagram of the system for assisting the pendulum movement of the legs.

FIG. 58: External profile view of the device according to the invention equipped with additional points of support for the body: support under the shoulders and by lateral handles on the saddle.

FIG. 59: External rear view of FIG. 58.

FIG. 60: External profile view of the device according to the invention with a first version on the telescopic device.

FIG. 61: External profile view of the device according to the invention with a second version on the telescopic device.

FIG. 62: External profile view of the link arm fitted with a joint whose vertical axis is close to the blockable joint.

DESCRIPTION OF THE PREFERRED EMBODIMENTS

Figure 12:
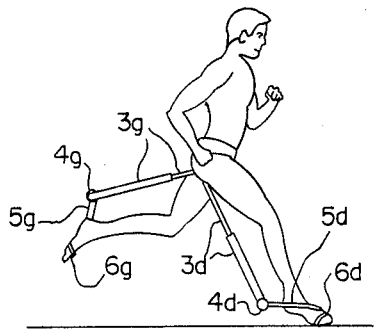
FIG. 12: side view of a man supplied with the device according to the invention at the moment his leg alights on the ground following a leap.

FIGS. 1 to 11 represent the whole of the device according to the invention in which appear:

The saddle 1 and its individual hip-fastening device 2. The telescopic device 3, blockable joint 4, link arm 5 and the joint secured to the front part of the shoe 6. On the views other than the profile view, the parts 3, 4, 5 and 6 bear left l or right r precision. FIGS. 1 to 3 show the complete device without a compressed fluid generator. The figures show that the telescopic devices 3 are situated behind the legs and are quite close to each other yet do not risk impeding each other. This does not limit the invention's possibilities which also includes cases where the distance between the two blockable joints would be much larger and would enable, for example, this joint 4 to be brought closer to the joint 6 so as to reduce the length of the link arm 5. In this case, the telescopic device, which, as shall be seen subsequently, may be curved or rectilinear, would partially pass the leg via the rear, but the whole device would still possess the same basic elements.

FIG. 4 shows the device with a compressed fluid generator 7 which in this instance is secured to the hip-fastening device 2 of the saddle, but this does not limit the possibilities of the invention. Indeed, as the functional link with the saddle and working cylinder of each telescope is effected by flexible pressure-resistant conduits (not shown on FIG. 4), the compressed fluid generator 7 can be totally separated from the saddle or its appurtenances. For example, it is possible to secure the generator 7 to the back of the individual, just like an item of luggage.

FIG. 5 shows a profile view of the device in a folded up position for transport or storage. It can be seen that, by virtue of the raising of the link arms 5, upon the maximum penetration of the telescopic device 3 and folding down onto the saddle of the hip-fastening device 2 supporting the compressed fluid generator 7, the whole fold up system takes up very little space and is easy to transport and set up. Where the generator 7 is not secured to the device 2, it can be fitted separately by disconnecting, by means of a fast joint, the two flexible feed conduits of the telescopic devices and a power socket providing functional electrical links.

FIGS. 6, 7 and 8 represent a first type of device 2 for securing the saddle to the hips. It is composed firstly of a part 2a connected to the rear of the saddle by a joint 8 whose axis is perpendicular to the center plane of the body and saddle. The role of the joint 8 is to continuously exert a thrust towards the top and front of the saddle, whilst permitting slight angular movements and folding up onto the saddle for arrangement. This part 2a preferably has an open-ended rigidity so as to keep the zone of joint 8 in a sufficiently rigid position without causing the individual discomfort. The zone situated behind will thus be more rigid than the zone in front which is closed with a belt buckle. The material comprising the part 2a may, for example, be a flexible thermoplastic such as PVC, either of open-ended thickness or reinforced in places by fabrics crossworked at 45°. The material can also be an elastomer such as polyurethane for exampe, also having an open-ended thickness and locally strengthened by fabrics crossworked at 45°. The part 2b is a flexible strap, possibly slightly elastic, which connects the front extremity of the saddle to a detatchable link on the belt buckle of the part 2a.

FIGS. 9, 10 and 11 represent a second type of device 2 for securing the saddle to the hips. It is composed of a wide belt 2c fitted at its base, preferably on the lower extensions situated on each side of the hips, with two joints 9 which serve as an point for two arms 2d which end in two joints 10 integral with the rear of the saddle 1.

The belt 2c may be made of materials of the type used for the first device 2 previously described, but the arms 2d are made of a rigid material, i.e. metal or rigid plastic such as, for example, polycarbonate. The inclination of the Joint 10, which can be seen on FIG. 11, is designed to obtain a slight folding of the arms 2d against the saddle. The inclination to be seen of the Joint 10 of the arms 2d on FIG. 9 shows that in this profile view, the angle constituted by the arms 2d with the top of the saddle 1 is constant. As a result, the points for fastening by the joints 9, which are situated above and in the middle of the length of the saddle in question, are sufficient to ensure that the saddle is kept in position during operation, a fortiori if the joints of the telescopic devices on the saddle are supplied with a three-gear stabilization system which will be described subsequently. These two devices for securing the saddle to the hips 2 may include variants and do not limit the possibilities of the invention. In particular, they may be adapted to various types of use of the device or to invalids. In particular, application of the force ascending on the saddle may be completed by the presence of belts passing over the shoulders and connected to the saddle.

Furthermore, as shall be seen subsequently, the saddle may be equipped with handles, as represented on FIGS. 58 and 59 These may serve as additional support for the body when the propulsion force is exerted by the device and thus reduce the force concentrated under the buttocks of the individual. At the same time, however, they may suffice for in particular all short-term uses in keeping the saddle in place with the hands in the absence of the device for securing 2 the saddle to the hips.

FIGS. 12 to 20 illustrate the overall mode of operation of the device according to the invention and its sound geometric compatibility with the human body in a variety of movements. In particular, FIGS. 12 to 17 represent several sequences, chronologically disposed, of the leaping movement which is a normal movement in which the bending after landing is somewhat accentuated so as to provide a better take-off and which includes a longer leap.

Figure 13:
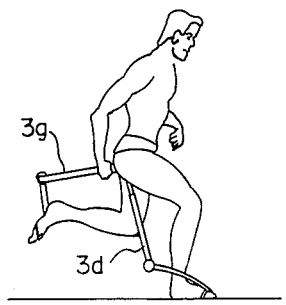
FIGS. 13 and 14: Successive chronological side views following the landing shown in FIG. 12
Figure 14:
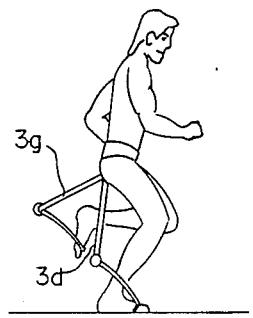
Figure 15:
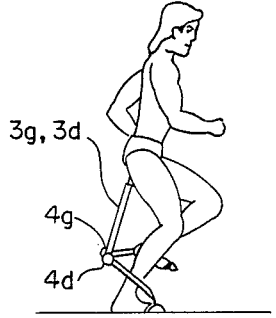
FIG. 15: View chronologically following view 14 at the moment the two telescopic devices are inside the same profile plane.

FIG. 12 shows the individual about to land on the right foot. FIGS. 13 and 14 show the bending phase after alighting. It can be seen that the bending here concerns the joint of the ankle and that of the knee, whilst in the movement without leaping, which can also be assisted by the device according to the invention, the distribution of the bendings over the natural joints may be slightly different. However, in all the cases, this bending phase corresponds to a reduction of the distance separating the joint 6d from the joint 11 under the saddle. FIG. 15 illustrates the moment when the left foot goes in front of the right foot which remains at the rear. This is also the moment when the righthand telescopic device 3d, which remains at the rear, is crossed by the lefthand telescopic device 3g which moves towards the front. The forces accomplished by the muscular system of the individual between the position shown in FIG. 12 and that of FIG. 15 are resistant or passive forces. They correspond to a fatigue which is useless for propulsion but are necessary to place the body in a favorable position or take-off position at the start of the propulsive phase. This is why one of the functions of the device according to the invention is to recuperate the energy called into play at this moment so as to restore it during the propulsive phase For this to occur, the individual must allow himself to sit on the saddle of the device and during this phase must only exert the minimum amount of muscular efforts required to ensure his equilibrium. The device stores energy either through the compression of its propulsion spring or by the compression of a bladder containing a gas, as shall be seen subsequently. In both cases, the alighting absorption function following the leap is also properly respected, thanks to the elasticity of the storage processes. Between FIGS. 15 and 16, muscular propulsion occurs and, in parallel with this, so does the propulsion effected by the device according to the invention since, as can be readily observed, the distance between the joint 6d and the joint of the telescopic devices on the saddle continuously increases during this period it is sufficient therefore for the extension engine force of the telescopic device to be applied during this phase. If this extension force is due to the spring-back of the propulsion spring, previously compressed in the phase between FIG. 12 and FIG. 15, no signal is necessary to trigger this force. If this extension force is due to the thrust of a fluid on a piston contained within the telescopic device 3d, the piloting device described further in this text causes the force to start close to the position described in FIG. 15 and stop close to the position described in FIG. 16.

Figure 16:
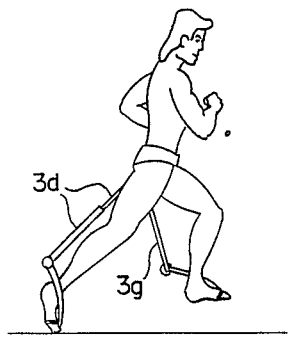
FIG. 16: Side view of the individual about to leap.

All the mechanical and muscular actions described between FIGS. 12 and 16 can be summed up by saying that the device is designed to aid the propulsive phase, at least the energy which it has taken from the passive or resistant muscular work during the alighting phase and possibly adds additional energy originating from a compressed fluid source. But in these two cases, the individual remains free to devote to the propulsive phase whatever muscular effort he chooses, this effort being more intense than normally as he has not had to exert more muscular effort on alighting. It will be observed that the propulsion assistance operation carried out by the device according to the invention does not result in additional stresses on the skeleton of the legs of the individual and his fragile pelvis joint. The force is exerted directly at the base of the spinal column where the use of movements on horseback has for a long time demonstrated the aptitude to receive significant forces: when a horse is trotting, its rider continuously receives forces capable of causing him to move out of his saddle. These forces are the maximum order of those forces which the device transmits under the saddle of the individual, but the control system enables the whole range of intermediate forces to be obtained. Moreover, as shall be seen at the conclusion of this text, various annexed systems enable the propulsive force between the base and top of the spinal column to be distributed at will.

In FIGS. 12 to 16, the blockable righthand joint 4d for the right leg device is in position blocked by its ratchet.

Figure 17:
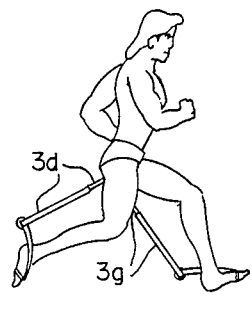
FIG. 17: Side view of the individual during the leap.

On the other hand, this joint 4d is unblocked immediately at the end of the operation represented on FIG. 16 so that on FIG. 17 it appears unblocked. Operations can be chronologically continued on this joint 4d of the right leg passing from FIG. 17 to FIG. 12 and involving the joint 4g of the left leg device. On FIG. 12, the joint 4g is unblocked, but the angle of the left link arm 5g with the left telescopic device 3g has still varied slightly in relation to the angle represented on FIG. 17 between the link arm 5d and the telescopic device 3d of the right side. But upon alighting, the individual must continue to move the left thigh towards the front, whilst keeping the left foot in a position which is sufficiently high so as not to risk coming up against an obstacle on the ground. The device according to the invention must not exert any force opposing this natural movement which might render the movement of the individual dangerous and awkward. This problem is overcome thanks to the unblocking of the joint 4g with freedom of movement in the joint 6g and very little inertia of the front part of the link arm 5g. Indeed, by presupposing that the telescopic device 3g has an adequate upward movement to enable the left foot to advance towards the front without striking the ground and unblocking the joint 4g, all the weight of the lower half of the telescopic device and all the weight of the link arm 5g would be constantly connected to the foot by the joint 6g. This would constitute high inertia which impedes and endangers equilibrium. Thanks to the unblockable joint 4g, the inertia of the telescopic device 3g is only experienced by the foot during the pendulum movement towards the front around the joint of the saddle. Now, firstly this pendulum movement occurs much more slowly than the bending of the left knee between FIGS. 13 and 14, and secondly the weight of the device 3g favors this movement since it takes place towards the ground as opposed to the preceding movement.

The essential role of the joint 4 is thus to ensure that the inertia influences of the device on the joint 6 of the foot and the upward movements of the leg are very slight. Moreover, as shall be seen subsequently, the unblocking of the joint 4 enables a relatively long time to be available in order to empty the working cylinder of the telescopic device 3 and to recuperate most of the expansion energy of the compressed gas which may occur there. Finally, thanks to the unblocking of the joint 4, the device takes up less space. On FIG. 15, the angle, then at a minimum and formed by the telescopic device 3g and the link arm 5g of the left leg, increases and reaches its maximum slightly before the left foot alights following the leap illustrated on FIG. 17 which returns to FIG. 12 by reversing the leg and so on.

Figure 18:
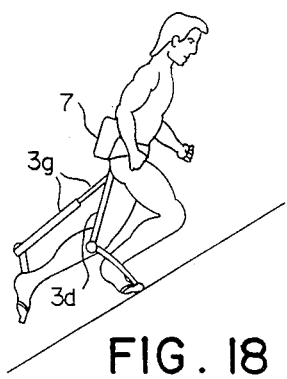
FIG. 18: Side view of a man supplied with the device in order to climb a steep slope at the moment the weight of his body has just rested on the front leg.
Figure 19:
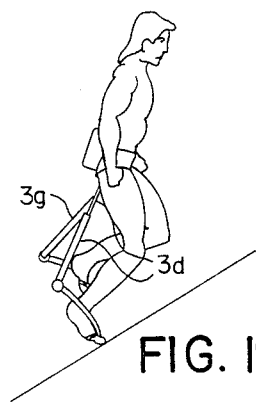
FIG. 19: View chronologically following FIG. 18.
Figure 20:
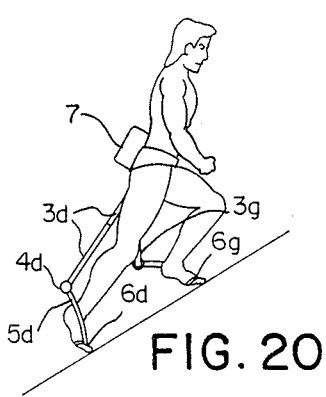
FIG. 20: View chronologically following FIG. 19. The propulsion by the back leg has almost finished and the individual has just put down his front foot without as yet having borne the weight of his body.

The joint 4 is equipped with a ratchet blocking device which enables the angle formed by the telescopic device 3 and link arm 5 to be increased, but which blocks the joint in the opposite case, irrespective of the angle attained. The unblocking system of the joint 4 consists of neutralizing the ratchet blocking so as to nevertheless enable the angle formed by 3 and 5 to be reduced. It is therefore essential for the unblocking system of the joint 4g to stop acting on the ratchet as soon as the telescopic device in question, the left in this case, moves forward past the telescopic device 3d of the other leg. Thus, regardless of the increase of the angle between 3g and 5g which will have been caused by the action of the left foot following this movement and before it touches the ground, the decreasing movement of this angle will then not be possible. The technical means required to attain this situation are described subsequently. FIGS. 18 to 20 illustrate a further mode of functioning of the device which corresponds to the ascent of a slope in the absence of any leaping movement. This is therefore a completely different method of application than that described in FIGS. 12 to 17, but it is also possible to climb slopes by leaps, that is to say via a mode which falls between the two modes described. In the absence of leaping, the only assistance possible in propulsion and compatible with a long autonomy is a fluid pressure being exterted on the piston contained inside the telescopic devices 3. The individual is thus diagrammatically represented on views 18 to 20 with a compressed fluid generator 7. As indicated earlier, this generator 7 may be hooked onto various points of the individual. However, the presence of an external box containing the generator 7 is not obligatory, except in the case of a motocompressor set, this not limiting the possibilities of the invention.

Indeed, it is possible to envisage, within the framework of the invention, a combustion principle inside even the cylinders contained inside the telescopic devices. This combustion may involve a fuel/air mixture according to a 4-stroke cycle which can be conceived by observing on FIGS. 12 to 17 the length variations of the telescopic devices 3 and by carrying out an analogy with a Beau de Rochas or Diesel cycle. In order to apply this combustion to the type of use described in FIGS. 18 to 20, it would, however, be necessary to envisage a two stroke cycle, which seems more difficult.

For all cases of use, this combustion may also be that of a chemical compound able to be air-sealed burnt and capable of generating a high gaseous pressure. I therefore suffices to automatically introduce and ignite a unit dose into the impervious expansible cavity of a telescopic device at the start of each propulsive phase and provide an escape of the gases at the end of the expansion stroke. These chemical compounds may be powders similar to those of fireworks and have a relatively slow combustion rate.

All these possible processes would, however, have very low energy efficiencies; thus the motocompressor sets are clearly cheaper to use and also offer much more flexible use conditions.

As shall be seen at the end of this text in the section relating to variants of the invention, if one confines oneself to very short autonomics of the device, other energy sources with high efficiency are possible and the box 7 is no longer necessary. FIG. 17 shows the individual having just borne the weight of his body on his right foot At this precise moment, the fluid pressure starts to be exerted on the piston of the righthand telescopic device 3d. This tends to increase the distance between the joint 6d of the right foot and the joint of the saddle and thus assist propulsion of the individual on the slope. FIG. 19 shows the right leg being propelled, assisted by the righthand telescopic device 3d. At the same time, the left leg of the individual ascends the slope, thanks to the unblocking of the joint 4g and, to a varying extent, thanks to the progressive drawing in of the telescopic device 3g away from the left leg which is in the course of evacuation. FIG. 20 shows that propulsion by the right leg is almost finished and the left foot is already in contact with the ground. The angle between the lefthand telescopic device 3g and the left link arm 5g has generally resumed the value it had in FIG. 18. However, it may be that on a very steep slope climbed slowly without leaping or with too long a stride towards the front or where a temporary obstacle is encountered by the left foot, this angle may not resume the value it had in FIG. 18. In these exceptional cases, the ratchet of the joit 4 prohibits the raising of the arm 5g, regardless of the angle, and the thrust due to telescopic expansion may nevertheless take place. The individual simply needs to terminate the propulsive stride of the left leg by means of a single muscular effort.

The expansion stroke of the telescopic devices, represented in this case by way of information and in no way limiting the possibilities of the invention and in the order of 25 to 30 cm for a man of 1.80 m, enables such a man to climb, for example, normal stairs with steps 18 cm in height.

FIGS. 21 to 24 describe a first mode of embodiment of the joints situated on the top of the telescopic devices 3 and on the saddle 1. It is possible to distinguish firstly the joint 11 whose axis is perpendicular to the center plane of the saddle and body and which connects the telescopic devices 3 to the saddle 1 and secondly, the joints 12 whose axis is roughly perpendicular to the center plane of the saddle. These joints 12 enable the telescopic devices 3 to be set apart from the center plane of the body, which enables the user to laterally spread his feet. On the other hand, the joints 12 are provided with a rotating stop device which prevents the base of the telescopic devices 3 from touching the center plane so that the two devices 3g and 3d never impede each other. It should be noted that the presence of the joints 12 does not limit the possibilities of the invention, since the device can fulfil its role without them, but with less comfort for the individual.

FIGS. 21 to 24 describe a system of joints 11 and 12 which also enables the telescopic devices 3 to be supplied with compressed fluid, but the principle obviously remains valid where a compressed fluid supply is not necessary.

The description solely concerns the right side of the device as the left side is identical.

Figure 22:
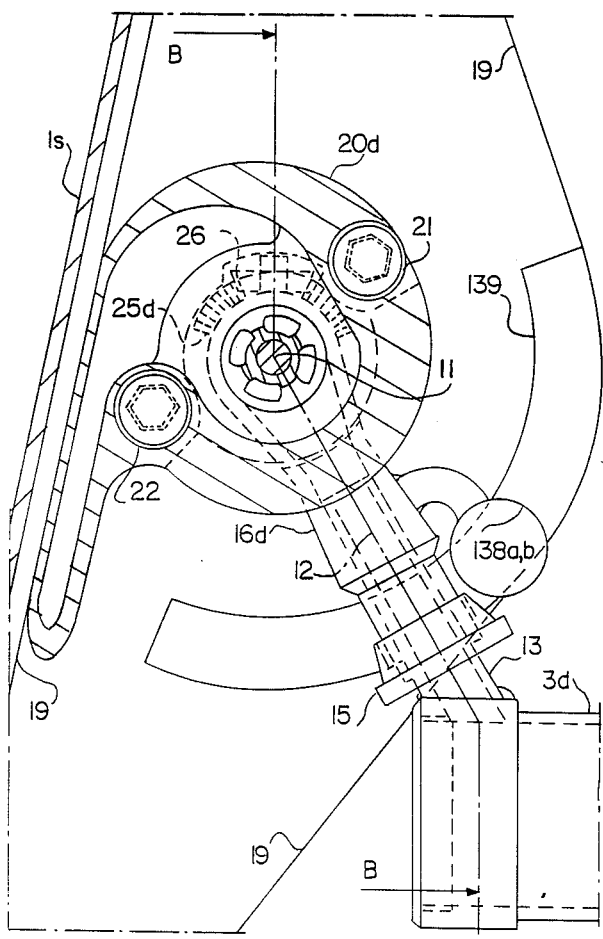
FIG. 22: Section along C—C showing the profile saddle with the first mode of embodiment of the upper joints of the telescopic devices.
Figure 23:
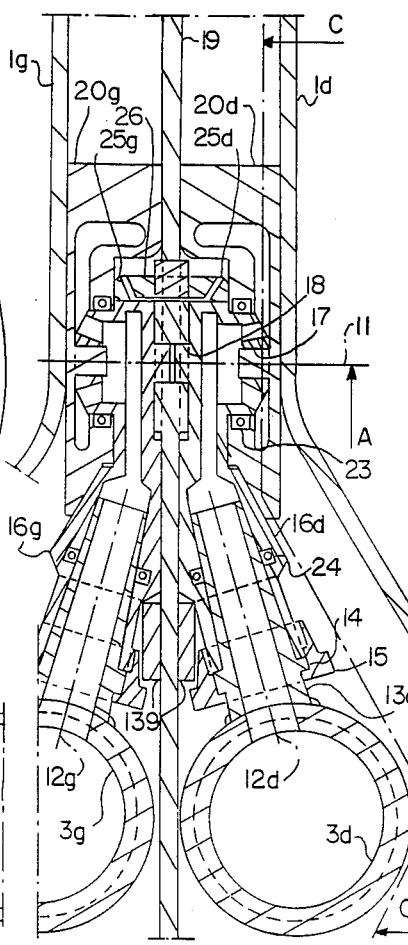
FIG. 23: Section along B—B showing the saddle seen from above with the first mode of embodiment of the upper joints of the telescopic devices.

FIGS. 22 and 23 illustrate the top of the telescope 3d to which is welded a hollow spindle 13 bearing a shoulder 14 and which holds a nut 15. The hollow spindle 13, which is the spindle of the joint 12, may rotate freely inside a bore of the connection part 16 which at its other extremity comprises a bore 17 and a full spindle section 18 which constitutes half of the joint 11 for the right side. The hollow spindle 13 is axially immobilized inside the part 16 by its nut 15 which is screwed onto the latter.

The full spindle section 18 rotates freely inside a bore made in an excessive thickness of the middle partition 19 of the saddle 1. The lateral walls of the saddle 1 are marked 1g and 1d on FIGS. 21 and 23 and the top of the saddle 1 is marked 1s on FIGS. 21 and 22. The bore 17 of the connecting part 16 receives a spindle section which is integral with a part 20d which is secured by the bolts 21 and 22 to the part 20g tightly gripping the central partition 19. The parts 16 and 20 include inner recesses for the passage of fluids and the joints 11 and 12 respectively have the gaskets 23 and 24. The part 20 quickly moves away from the center plane and towards the back of the saddle where it forms the connections of supply channels so as to free the space under the saddle inside the pendulum clearance zone of the tops of the telescopic devices 3.

The parts 16g and 16d are provided with a conical annular gear sector 25g and 25d centered around the axis of the joint 11 and cooperate with a conical cog gear wheel 26 which turns freely on a spindle welded onto the middle partition 19. In this way, the axis of this cog wheel and the saddle integral with it retain the same angle with the bisectrix of the angle formed by the connecting parts 16d and 16g and thus with the telescopic devices 3d and 3g.

Now, it can be seen from FIGS. 12 to 20 that the angle formed by the bisectrix of the angle of the two telescopic devices 3 with the trunk varies slightly. Consequently, the toothed sectors 25d and 25g and the conical gear wheel constantly keep the top 1s of the saddle in a favorable direction. The use of these sectors 25 and conical gear wheel 26 is not obligatory, nor does it limit the possibilities of the invention, but it presents, amongst other things, the advantage of being able, if necessary, to position the axis of the joint 11 at a sizeable distance behind or in front of the point of the saddle which occurs under the center resulting from the vertical thrusts which the body exerts on the latter. Thus, for example, it would be possible, in the case of FIGS. 22 and 23, to place the joint 11 much closer to the longitudinal axis of the telescopic devices 3, without the saddle sinking towards the front under the weight of the body.

Figure 24:
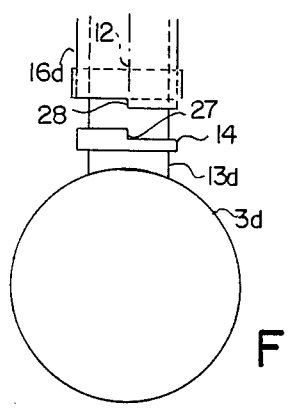
FIG. 24: View from above of a telescopic device showing the stop system established on an upper joint of the latter in the case of the first mode of embodiment.
Figure 21:
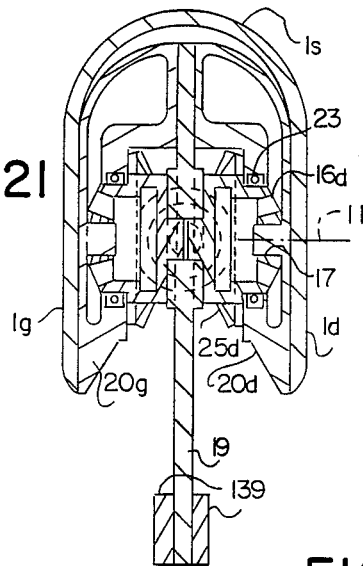
FIG. 21: Section along A of the central part of the saddle as seen from the rear and showing a first mode of embodiment of the upper joints of the telescopic devices.

FIG. 24, which describes the principle of the stop on the spindle joint 12, shows the set of notches 27 made in the shoulder 14 of the hollow spindle 13d. This set of notches cooperates with a set of notches 28 in the connecting part 16d when the hollow spindle 13d is thoroughly driven into the part 16d and is axially maintained by the nut 15 (not illustrated).

FIGS. 25 to 28 describe a second mode of embodiment concerning the joints situated on top of the telescopic devices 3 and saddle 1. From these figures, it can be seen that the fluid supply of the telescopic devices 3d and 3g is ensured independently of the joints 11 and 12 through the flexible channels 29g and 29d.

The joints 12g and 12d are situated on the top of the telescopic devices 3d and 3g, their axes being as far as possible from the center plane. They consist of two screws 30 and 31 whose extremity is an unthreaded spindle. These screws 30 and 31 are screwed into the connecting part 32d between the joints 11 and 12 and their unthreaded extremity passes through an unthreaded length of the part 32d and embeds itself in a bore integral with the telescopic device 3d. The stop of this joint 12, preventing the telescopic device 3d from going past the center plane of the saddle, is a partition 33 of the connecting part 32d beneath which the top of the device 3d comes to rest.

The joint 11 consists of a hollow tube 34 welded onto the center partition 19 whose extremity freely turns inside a bore of the connecting part 32d. The inside of the tube 34 is threaded and receives the axial immobilization screws 35.

Finally, this second mode of embodiment can also be provided with the two sectors 25 and cog wheel 26 described for the first mode. The two modes for the embodiment of the joint on the saddle and the joints on the top of the telescopic devices which have been described do not limit the possibilities of the invention; in particular, it is possible to combine their technical aspects in other ways or, conversely, to further dissociate the various functions. Moreover, the axis of the joint 11 has been presupposed to be rectilinear and common to the joint of the left and right telescopic devices. But it is also possible to conceive that the axis 11 has a right part and a left part not quite perpendicular to the center plane of the saddle for various reasons, whilst being symetrical in relation to this plane. This disposition could very possibly constitute a technical choice. The fundamental special feature of the axis 11 will thus, in all cases, be that of being roughly perpendicular to the center plane of the saddle and the body.

FIGS. 22, 23, 26, 27 and 28 also describe parts required for piloting. These parts will be examined later in the text.

The saddle 1 has a resistant structure which organizes itself here around the sturdy center partition 19, but it is also possible to envisage other devices, provided they enable the top of the telescopic devices 3 to return at the end of the pendulum movement around the joint 11 as high as possible and thus very close to the surface 1s of the saddle.

FIGS. 29 to 34 describe the telescopic devices 3 in various contexts. In all the cases described in FIGS. 29 to 34, the telescopic device is compsoed of two concentric tubes, but a cylindrical section in no instance limits the possibilities of the invention: as illustrated in the lower part of FIG. 33, rectangular, square and special sectional tubes can be used; it is also possible to use inserted sliding profiles whose perimeter is not closed. The notion of telescope includes all shapes which can be fit into each other and slide axially. Moreover, as mentioned above, the axis of the telescope does not have to be rectilinear: it is possible to use a curved telescope characterized by a constant radius of curvature identical for the two inserted parts, the notion of telescopic device denoting the telescope and its annexed elements and permitting firstly sliding in the presence of a torque and secondly, the application of an extension force by a spring or fluid and finally possible return springs.

Furthermore, the devices described in FIGS. 29 to 34 always exhibit their outer female tube at the bottom. This disposition is preferable to the inverse disposition as the male tube, being more fragile, is less vulnerable close to the saddle and in addition, it is easier to secure the blockable joint 4 to the female tube than to the male tube. However, this disposition does not limit the possibilities of the invention which accordingly includes the opposite possibility.

FIGS. 29 to 31 relate to a first telescopic device whereby the mode for exerting the extension force is due to the action of a compressed 30 fluid on a piston. If the imperviousness quality of the piston is sound, the fluid could be a liquid or gas, but if it is merely passable, the fluid may only be air, leaks of this being being of only slight significance. In FIGS. 29 to 31, the inner cylinder, into which slides the piston 36 equipped with the plastic sealing washer 37, is the inner wall of the upper part 3s of the telescopic device. It is also possible to have an additional cylindrical part concentric to the part 3s to accomodate a piston with a small diameter and operating at a higher pressure. The lower part 36b of the piston acts as a stop to limit the maximum extension. The piston 36 is extended by an extension piece 36r secured by a screw 38 to the base of the lower or female part 3i of the telescopic device 3.

A return spring 39, which tends to reinsert the parts 3s and 3i of the telescope in the absence of forces greater than its own, takes support on a plunged boss 40 situated towards the lower extremity of the part 3s of the telescope and acts on a plunged boss 41 situated on the upper part of the piston 36.

The sliding of the upper male 3s and lower female 3i parts in the presence of a torque is ensured by two sets of needle or roller bearing castors. The upper set of castors, the axes of which are integral with the lower female part 3i of the telescopic device, is secured to the upper extremity of this part 3i and includes three castors sectionally visible in the top axial view contained on FIG. 30.

There are two main castors 42 and 43 whose axes are perpendicular to the axis of the telescope and inclined about 60° in relation to the center plane of the body, the contact surface of the castors being tangential to the male or upper part 3s of the telescope. There is also a secondary castor 44 whose axis is perpendicular to the axis of the telescope and roughly perpendicular to the center plane of the body. This system of 3 castors keeps the tubes 3s and 3i apart from each other, even in the presence of a significant radial force. The main torque force is received by the castors 42 and 43 which are disposed at the front of the telescope in relation to the individual.

The lower set of castors whose axes are integral with the upper or male part 3s of the telescopic device is secured to the lower extremity of the part 3s and includes three castors sectionally visible in the top view contained in FIG. 31.

There also exist two further main castors 45 and 46 and another secondary one 47, the disposition of whose axes is symetrical with that of the upper castors 42 to 44. The main castors, which receive the torque force, are then disposed at the rear of the telescopic device 3 in relation to the individual and roll over the inner part of the lower or female tube 3i of the telescope.

The cross section of the extension piece 36r of the piston 36 is visible on FIG. 31 and it can be seen that it enables the lower tube 3i of the telescope with which it is integral to rotate significantly in relation to the upper tube 3s integral with the castors 45 to 47, without it entering into contact with such castors. This gives an added degree of freedom to this type of telescopic device, namely a limited rotation around its axis. This enables the individual to carry out a vertical axis rotation with his foot.

Having regard to the high torque forces to which the telescopic devices 3 are subjected, it is essential that the tubes 3s and 3i and the castors be made of steel offering very high mechanical performances, which endows them with a long period of service life and enables them to be as light as possible.

Other elements visible on FIGS. 29 and 31 shall be described in the section relating to piloting.

The top of the part 3s is not illustrated but it may, without this being in any way limitative, be one of the types represented on FIGS. 22 to 28.

FIG. 32 represents a telescopic device 3, the tubes 3s and 3i and six sliding castors of which are identical to those described on FIGS. 29 to 31.

Its mechanical operation is due to a high-powered spiral spring 48 which leans against the head of a piston 49 extended by an extension piece 49r similar to the extension piece 36r of the preceding case. The other extremity of the spring 48 takes support under the cover of the upper part 3s of the telescopic device where there is a prestressing control system composed of a screw and a nut There is no return spring as the spring 48 is prestressed which, in the absence of external forces at the telescope, brings the lower extremity of the piston 49 back into contact with a stop integral with the lower extremity of the male or upper tube 3s of the telescope This stop may be one of the castors 45 or 46. The prestressing of the spring 48 may possibly be very slight or nil.

In FIG. 32, the raising of the foot following a propulsive phase is therefore merely due to the angular movement towards the top of the link arm 5 resulting from the unblocking of the joint 4.

However, other means exist to bring the force of the spring 48 into play, thus enabling the telescope 3 to be shortened following the propulsive phase. The disposition described in FIG. 32 for the spring 48 does not therefore limit the possibilities of the invention.

Figure 33:
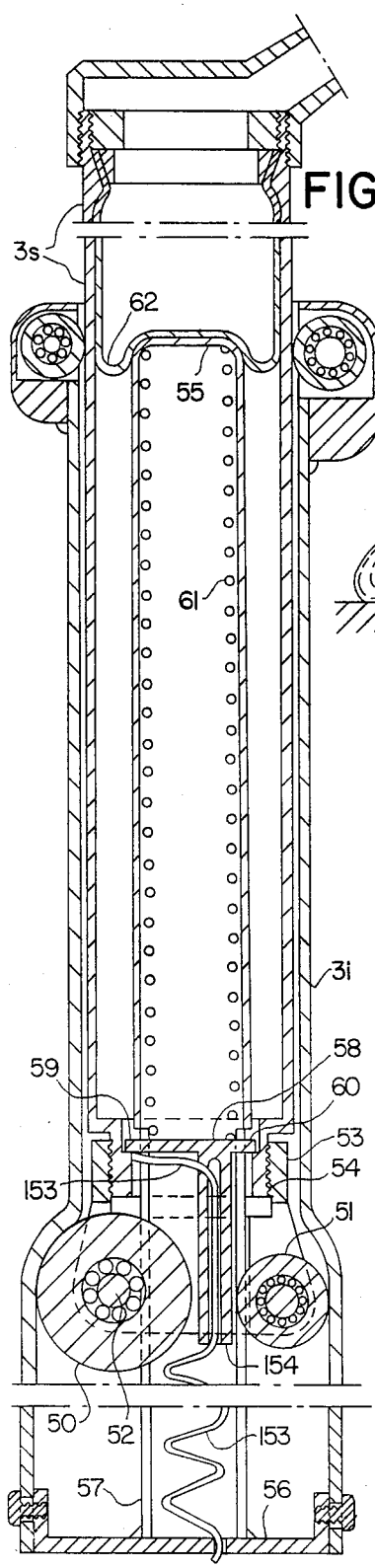
FIG. 33: Profile cross section of a third telescopic device.
Figure 34:
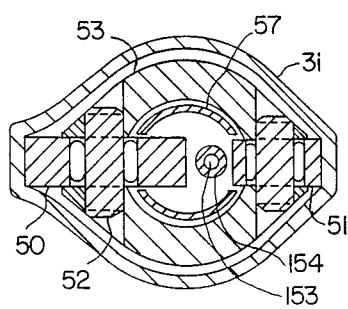
FIG. 34: Top cross section of the third telescopic device showing the lower castors.

The telescopic device represented on FIGS. 33 and 34 possesses a set of three upper castors identical to the set described on FIGS. 29 and 30.

On the other hand, its lower guidance only includes two castors 50 and 51, the largest of which, placed at the rear of the telescope, receives the torque forces. These castors roll over the inside of the female or lower part 3i of the telescope whose section visible on FIG. 34 is extended roughly parallel to the center plane. This enables a castor 50 to be used which has a relatively small diameter. The spindle 52 of this castor is no longer directly integral with the lower extremity of the tube 3s, but is fixed into a part 53 which is connected to the part 3s by means of a flat thread screw cutting 54. Since the screw cutting does not constitute a stop, the part 53 can rotate freely in relation to the part 3s. The flat thread does not limit the possibilities of the invention, its purpose being to rotate more easily than a V-thread. The disposition described is suitable for transmitting forces exerted on the head of the piston 55 as far as the bottom 56 of the lower part 3i of the telescope. Indeed, the lower extension piece 57 of the piston 55 is then a tube or rod split diametrically so as to allow for, with a small clearance, the passage of the castors 50 and 51. When the lower part 3i of the telescope is rotating in relation to the upper part 3s, the split tube 57 and the castors 50 and 51 are thus driven simultaneously, in contrast to the cases concerning the castors 45, 46 and 47 and the extension piece 36r or 49r.

A part 58 also slides through the slits of the tube 57 and its two protuberances 59 and 60 will take support on a bore with a shoulder made in the lower extremity of the part 3s.

Thus, the part 58 is integral with the rotating tube 57 and with the translation part 3s. It serves firstly as a support for the return spring 61 of the telescopic device and secondly for the passage of pilot wires, as shall be seen subsequently.

The device for exerting the extensive force of the telescopic device appearing on FIG. 33 is a concentrically unwindable cylindrical diaphragm 62 tightly secured to the top of the tube 3s as can be seen on FIG. 33. The advantage of this process is the total absence of any leakage and it is particularly suitable for the use of liquids under pressure. The diaphragm 62 is an elastomer diaphragm, preferably reinforced with organic or mineral fibers and preferably in the form of a cylindrical fabric whose threads constituting the generators are in the majority and whose circular directrix threads are in the minority or are made of elastomer. In this way, the diaphragm 62 resists strong axial forces and can easily undergo a concentric rolling involving two significantly different diameters.

The telescopic devices of FIGS. 29 to 34 are all shown in the maximum extension position so that their return spring 39 or 61 is compressed to the maximum and the distance between the set of upper castors and the lower set is minimal.

As mentioned above, the guidance systems described enabling the various elements of the telescope to slide into each other and the means described for exerting a mechanical extension action, by means of a spring or compressed fluid, and the means described to permit the telescopes to rotate axially do not limit the possibilities of the invention. The systems described may firstly be combined in different ways. Secondly, they may be added to by:

telescopes comprising more than two sliding inserted elements, guidance systems comprising more or less castors than is specified, ball circulation guidance systems or systems with balls guided by intermediate retainer cages, guidance systems replacing the castors or balls slightly loaded by friction parts, etc.

various internal dispositions for the pistons required to transmit a fluid pressure and comprising, for example, valves and reservoirs inside the telescopes in order to limit the transfers of fluids in certain configurations, etc.

different uses of the spring required to store and restore energy, etc.

Figure 35:
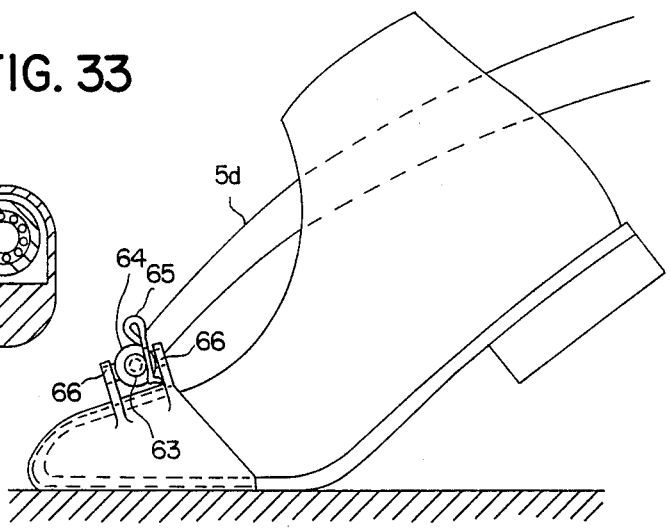
FIG. 35: Profile view of a link arm and a shoe equipped with a joint in its front part.
Figure 36:
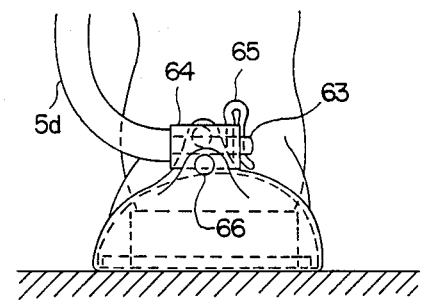
FIG. 36: Front view of a link arm and a shoe fitted with a joint.

FIGS. 35 and 36 represent a mode, also not limiting the possibilities of the invention, for embodying the joint 6 on the front part of the shoe.

Figure 37:
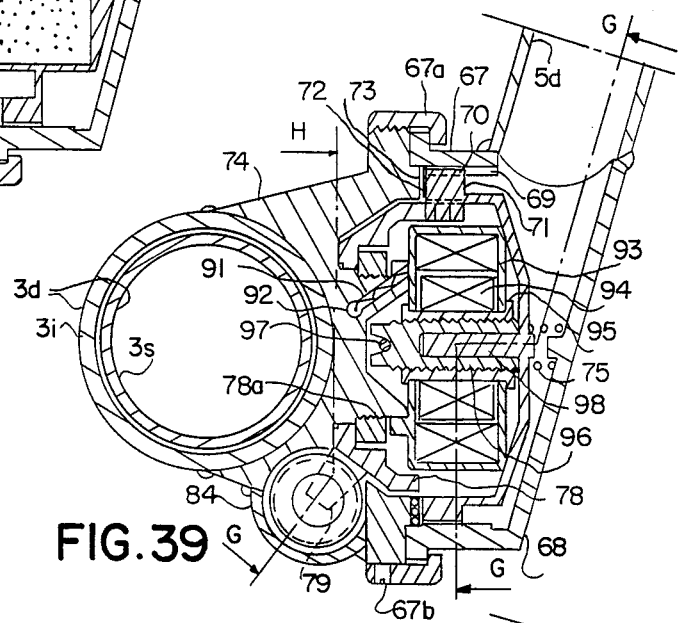
FIG. 37: Top view of a shoe, link arm and section of a telescopic device.

If one considers the top view of the foot shown on FIG. 37, the sought-after aim as regards the joint 6 is to authorize wide angular movements around an axis roughly perpendicular to the center plane of the body and to prohibit vertical axis rotational movements which could result in the arm 5d being impeded by the ankle, shoe or base of the calf. Moreover, and according to the most current uses reserved for each type of device according to the invention, it is sometimes useful for the joint to authorize a rolling movement of the foot of limited amplitude. This movement is effected around a roughly longitudinal axis of the foot. The rotation of the foot around a horizontal axis roughly perpendicular to the center plane of the body and thus roughly perpendicular to the longitudinal axis of the foot and roughly parallel to the ground is obtained by means of the spindle 63 extending the link arm 5 and which can rotate freely inside the bore of a cylindrical part 64. The mounting and dismounting of the spindle 63 inside the part 64 are effected immediately by lifting or driving into a hole of the part 64 the pin 65 which axially immobilizes the spindle 63, thanks to the spindle having a circular groove.

It needs to be stated here that in order to be equipped with the device, the individual starts by putting on the shoes fitted with the part 64. Then he places the device vertically on the ground, the device taking support on the base of the telescopic devices 3 and joints 4. He then sits on the saddle and fastens the saddle hooking belt. Finally and still in the seated position, he drives the spindles 63 of the link arms 5 into each of the parts 64 and drives in the pins 65.

The cylindrical part 64 has two lateral shaft sections 66 which delimit a rotational axis perpendicular to the bore of the part 64 and roughly longitudinal in relation to the foot. These two shaft sections 66 are each housed inside a bore of a part integral with the shoe and which enables them to rotate freely with a limited angular value, which authorizes a slight rolling of the foot and renders movement more agreeable to the individual. However, if the individual is fitted out with additional accessories, such as ice skates or two-wheel roller skates, he may wish to totally block this rolling motion with a bolster or shim placed under, for example, the part 64. As in all cases the rolling motion amplitude authorized by the device is slight, this helps the individual on varied terrain to avoid sustaining a broken ankle, thanks to the telescopic device and the torsion rigidity of the arm 5.

The securing of the bores receiving the shaft sections 66 onto the front part of the shoe can be effected in many ways.

FIGS. 35 and 36 represent one mode of fastener consisting of a hollow part, preferably metal or hard plastic, encompassing the extremity of an ordinary shoe and fixed under the saddle. The invention may also include other dispositions, such as, for example, the securing of the spindle to the saddle, especially where the individual is generally simultaneously using skates and does not require any rolling motion. Finally, the spindle 63 can be fixed directly into the accessory, skate or ski, which is possibly used. Moreover, the implantation of the spindle 63 in relation to the length of the foot varies depending on usage. It also takes account of the flexural strength of the shoe. The only common point is that this implantation occurs in the front part of the foot or possibly in front of the latter so as to affect the largest possible geometric deformation during extension of the leg and foot which cause the propulsion of the body.

The shape of the link arm 5d, represented in the form of a top view on FIG. 37 and a profile view on FIG. 2, in relation to the foot is conceived according to the following elements: compatibility with the spatial requirements and displacements of the lower part of the leg and foot, which results in it being preferably disposed outside the legs and not between the legs and in adaptation of the sections to the value of the local bending moment. Furthermore, the arm 5 has in profile a preferably curved form with concavity towards the ground so a to make it less vulnerable to obstacles. The material constituting the link arm 5 may be a mechanical high-performance steel or light alloy or an organic matrix composite, provided that in these latter two cases, the link with the joint 4, and in particular with the blocking ratchet, is made up of a high-performance added steel part, the spindle 63 of the joint 6 also being required to be made of steel.

This definition of the link arm 5 does not limit the possibilities of the invention and it may be that the shapes of the latter need to be adapted, either to the preferential use of an accessory such as a skate, ski, etc., or to a special type of infirmity.

FIGS. 38 to 45 describe modes for embodying the blockable and unblockable joint 4. The joint described is in all cases a right joint of the individual which is symetrical with the left joint.

On the telescopic device 3, the general implantation of the joint 4 is described on FIGS. 2, 3, 4, 5, 37, 51, 56, 58, 59, 60 and 61. However, this implantation does not limit the possibilities of the invention as it is obvious that the joint 4 can firstly be placed slightly above the lower extremity of the telescopic device and secondly it can be placed more in front or at the back, in relation to the direction of the step of the individual, of the position in which it is represented.

In these cases and if the telescopic devices 3 remain in the same position behind the legs, the link arm 5 would simply be shorter or longer and that part of the joint 4 integral with the telescopic device would be connected to the latter via a rigid arm. With a suitable shape of link arm, it is also possible to use a U-joint traversed by a spindle whereby the extremity of the joint 5 forms the U and the telescopic device occurs in the center of the U. All sorts of constructive variants are thus possible within the framework of the overall invention.

Figure 38:
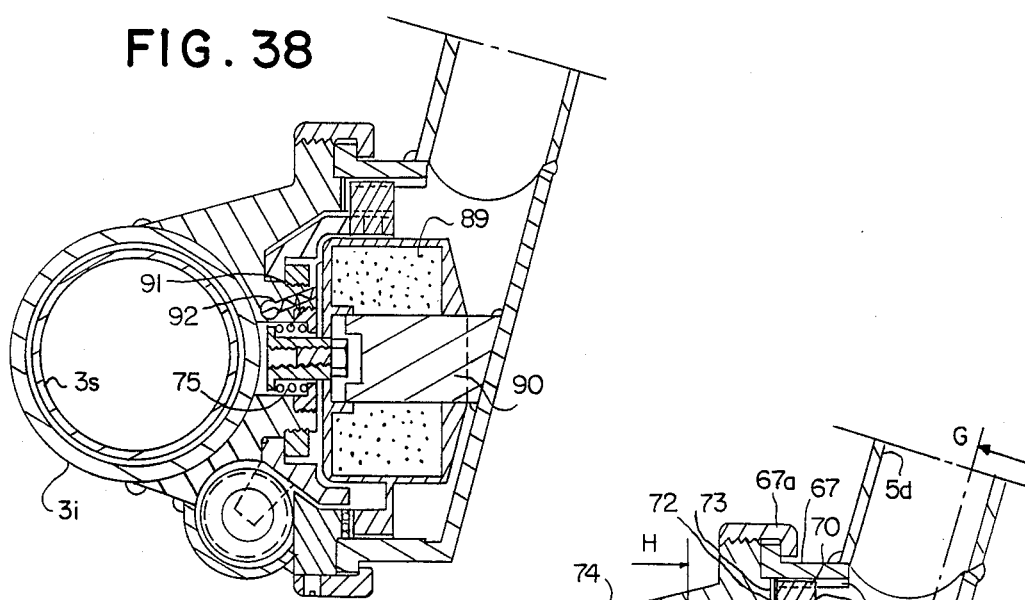
FIG. 38: Section of a blockable joint with a first unblocking mode.
Figure 39:
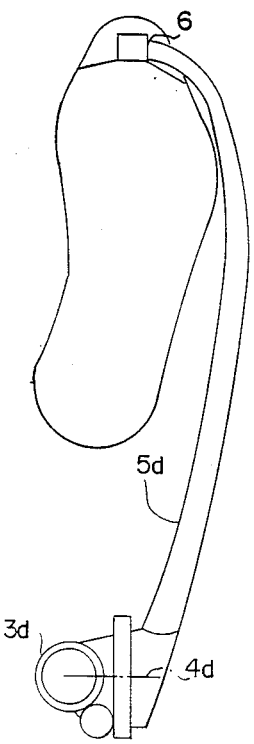
FIG. 39: Section of a blockable joint with a second unblocking mode.
Figure 40:
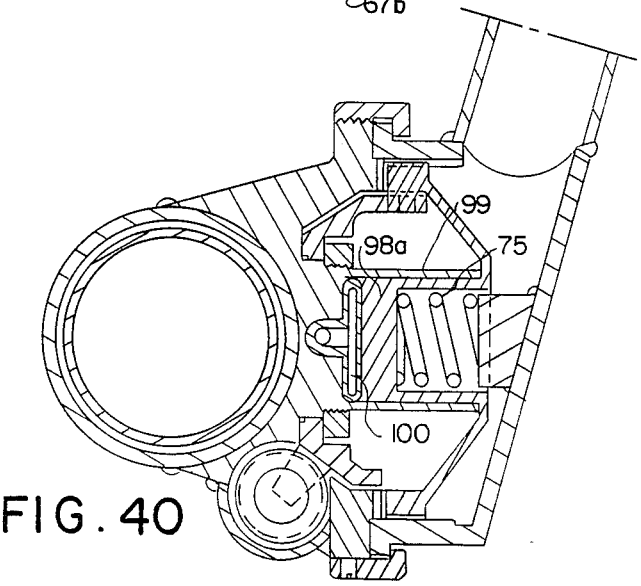
FIG. 40: Section of a blockable joint with a third unblocking mode.

FIGS. 38 to 40 describe the blockable joints 4. These have common parts, also described on FIGS. 41 to 45, and only differ as regards the unblocking activation mode. Certain roles of the joint 4 have already been mentioned earlier, but they are repeated and supplemented below:

During the descent of the foot accompanying that of the link arm 5 and the opening of the angle which the arm 5 forms with the telescopic device 3, the joint 4 prohibits the reciprocal free angular movement at any moment, thanks to a ratchet propelled by a spring. When the foot rests in front of the body on the ground and until all effort has ceased, i.e. almost when the foot situated at the rear starts to come away from the ground, the joint 4 remains blocked and all the forces undergone or exerted by the telescopic device pass by it. Upon cessation of the forces, the joint 4 must enable the foot to be instantly raised again, thus reducing the angle formed by the link arm 5 with the telescopic device 3. For this to occur, the ratchet system must be temporarily put out of action. Furthermore, the joint 4 is equipped with a adjustable stop which enables the maximum opening angle between the link arm 5 and the telescopic device 3 to be adjusted so that, when this angle is reached, the force created by the foot when being lowered towards the front is transmitted to the telescopic devices 3 and then extends the latter whilst compressing their return spring. The adjustment of the stop enables, amongst other things, the device to be adapted to an certain extent to the size of an individual.

However, so as to provide the individual with more comfort and to avoid sudden mechanical shocks, the stop is fitted with a prestressed spring.

In order to further compress this spring with the stop, the descending force to be applied by the foot through the joint 6 is greater than that required to extend the telescope to the maximum and thoroughly compress its return spring. The compression of the stop spring thus represents a certain overshooting of the maximum angle between the arm 5 and the telescope 3 which occurs through adjustment of the stop, this overshooting only being able to take place if the telescopic device 3 is already in the maximum extension position.

Another role of the joint 4 is to see to it that the ratchet system is unable to function whilst the stop spring is compressed and that accordingly, the opening of the angle of the arm 5 and telescope 3 exceeds a value provided by the selected stop adjustment. This latter role gives rise to certain advantages concerning the adaptability of the device according to the invention to various sorts of reliefs, speeds, types of movement—with or without leaping—and various types of additional accessories, such as skates, etc. Indeed, this latter improvement in certain cases enables the mechanical assistance being given to the propulsion of the leg to be stopped on average shortly before the end of the rear stride, if one so desires, and to finish the stride without mechanical assistance. In this way, the end of the stride is experienced more gently and naturally by the individual.

Moreover, and especially if the spindle 11 of the joint under the saddle is situated almost behind the latter, the extension of the telescopic device during the front stride of a leap on flat terrain is generally slightly larger than during the rear stride. But, with the ratchet being put out of action during the violent pressure of the stop spring, this aspect does not constitute a drawback if the difference in extension values is absorbed by the angular course of the link arm 5 beyond the stoppage.

The means enabling the blockable joint 4 to fulfil the roles assigned to it are the following, but these do not limit the possibilities of the invention. Other ratchet systems may be used as well as other systems which render the ratchet inoperative. Moreover, the adjustable and damping stop system also capable of rendering the ratchet inoperative is a very useful improvement, but is not absolutely obligatory. The only obligatory aspect is to have available a device for blocking and unblocking this joint.

The parts common to the various types of joint 4 described will be examined on FIGS. 39, 41, 42, 43, 44 and 45. FIG. 39 shows the arm 5d connected, for example by weld, to a cylindrical seat 67 fitted with a closing plate 68. There is also a sectional view of this seat 67 on FIG. 41. The seat 67 comprises a plunged boss on which a nut 67a takes support, screwed onto the other part of the joint, but not blocked, and locked by the screw 67b. As can be seen on FIG. 37, it is an advantage for the plane of the joint 4 to pass through the joint 6 as thus all the mechanical forces will remain within this plane. The seat 67 is fitted with an axial toothing 69 which cooperates with an axial toothing 70 of the cylindrical ratchet 71 visible on FIGS. 39, 41, 43 and 44. The ratchet 71 is thus able to slide axially into the cylindrical seat 67 and transmit to it a very high torque in the absence of any axial movements. The cylindrical ratchet 71 also bears, on one extremity face, a disymetrical profile radial toothing 72 which cooperates with an identical toothing 73 cut on the seat 74 of the joint 4 which is integral, by weld for example, with the lower part 3i of the telescopic device. The disymetry of the toothings 72 and 73, kept in contact by the spring 75 which exerts an axial thrust on the ratchet and its extension, authorizes the rotation of the joint 4 in one direction and not in the other, as explained earlier: with the individual standing, the arm 5d may therefore be lowered and cannot rise again.

It should be noted that the axial toothings 69 could be integral with the seat 74 and the radial toothings could, conversely, be integral with the seat 67. This disposition is within the sphere of the invention.

Another function of the cylindrical ratchet 71 to to transmit the angular stoppage forces of the joint 4 thanks to three uneven sections 76. These cooperate with three uneven sections 77 of a part 78 visible on FIGS. 39 to 45 with a circular general section which can rotate freely inside the seat 74 to which it is linked axially by the nut 78a. The circular ratchet 71 thus tends to rotate the part 78 as soon as the uneven sections 76 encounter the uneven sections 77.

The part 78 is supplied with a snug 79 visible on FIGS. 39 and 42 and whose role is to lean against the stop 80 which is a cylindrical cage keeping the stop spring 81 in the prestressed position. The base of this spring rests against a nut 82 cooperating with a screw rod 83 to which it communicates the thrust of the snug 79 and this rod 83 transmits it to the cylindrical cage 84 welded onto the seat 74. By operating the wheel head 85, it is possible to move the initial point of support between the snug 79 and the stop 80 towards the top, which affects the angular position of the stoppage. FIG. 42 represents the stop 80 in the maximum adjustment position towards the bottom.

The compression of the spring 81 which causes the axial displacement of the nut 82 in relation to the stop 80 thus enables the part 78 bearing the snug 79 to temporarily continue its rotation, thus opening further the angle formed by the telescopic device 3 and the link arm 5.

It has been seen earlier that the part 78 rotates freely inside the seat 74. Consequently, when the uneven sections 76 of the cylindrical ratchet 71 come into contact with the base of the inclined plane 86 of the uneven sections 77, the sole axial pressure force exerted by the spring 75 on the ratchet 71 will be sufficient to cause the part 78 to be rotated by the three uneven sections 76 without the latter ascending the inclined planes 86. This rotation of the part 78 will bring its snug 79 into contact with the stop 80. At this precise moment, the axial thrust due to the spring 75 will no longer be sufficient to enable the part 78 to be rotated and the three uneven sections 76 will ascend the three inclined planes 86 as far as the surfaces 87 and then come to a stop on the perpendicular planes 88. The transmission of a sizeable torque by the ratchet to the stop will then again be possible, but the The slide valve 107 is equipped at each of its extremities with a spring 118 whose length, in the absence of contact, is known with precision, and an uneven section 119 which serves to propel the slide valve 106 in one direction or the other.

A fourth throat 120 encompasses the slide valve 106 and can communicate with the latter. It is connected via the pipe 121 to a tank 122 at atmospheric pressure. From this tank, a pipe 123 extends and terminates in the pipe 115 via a reverse-lock valve 124. The pipe 115 is also connected to the inlet of a damping and partial energy recovery reservoir 125 which possesses a ductile diaphragm 126 behind which is the compressed air. Finally, the pipe 115 is connected via the pipe 127 to the inlet of the compressor 104.

The general functioning, and of the distributor in particular, will be better understood by considering the four views 46 to 49, firstly for a method of application relating to the device and described on FIGS. 12 to 17, and then for a method of application relating to the device and which is described on FIGS. 18 to 20.

FIG. 12 corresponds to the position of the slide valves 106 and 107 represented on FIG. 46: the pipe 110g receives the liquid originating from the left telescope 3g and the slide valve 106 sends it via the pipe 121 into the atmospheric pressure tank 122, thus offering no resistance to the ascending of the left telescope which is followed up on FIGS. 13 and 14 and as far as FIG. 15 under the action of its return spring 39 or 61.

The pipe 11d, which has enabled the fluid coming from the tank 122 to be sent to the right telescope 3d during its extension prior to FIG. 12 via the pipe 123, reverse-lock valve 124, pipe 115, throat 114, passage 116, throat 117, slide valve 106 and throat 112, starts from FIG. 12 up to FIG. 15 to receive the fluid originating from the right telescope which contracts and sends it into the pipe 115 where one part will be sucked in by the compressor through the pipe 127 and another part will enter the damping/recovery reservoir 125 where it will compress the compressed air by distorting the diaphragm 126. The compressed air spring thus has the role of cushioning the landing and storing the quantity of fluid under pressure abruptly driven back by the telescope 3d which the compressor could not pump quickly enough, but which it will pump immediately afterwards.

FIG. 15 corresponds to the moment the slide valve 107 passes from the position it occupied on FIG. 46 to that it occupies on FIG. 47. There has simply been a cutoff of the current of the electromagnet 108 which was keeping the spring, on the left of the figure, compressed. The release of the spring has provoked displacement of the slide valve 107 without displacing the slide valve 106. Thus, the passage 116 and throat 117 are no longer in communication with the pipe 115 but with the pipe 113, which enables the liquid under pressure to be sent into the telescope 3d and enables the individual to obtain the moving force for assisting propulsion by means of the right leg.

The buffer reservoir 103 may, if necessary and in a very simplified way, contain two ductile diaphragms 128 and 129, behind which are respectively the compressed air and a gas or gas mixture made up of freon compounds for example, which is/are present in temperature and pressure conditions closely approximating their liquid-gas equilibrium. Thus, the role of the air is to make use of the energy storage spring according to the law $PV = RT$ which, with the buffer reservoir being small and therefore light, results in a decreasing evolution of the pressure being exerted on the pistons as they are gradually extended. The role of the mixtures of freons or other gases in temperature and pressure conditions approximating their liquid-gas equilibrium is to reduce the pressure deviations established according to the extension of the telescopes. Thus, according to the preferential usages ascribed to a certain type of device according to the invention, the most desirable law of pressure variation can be brought into play to ensure comfort and effectiveness.

FIG. 16, which shows the end of the propulsive stride made by the right leg, corresponds to the passage to the slide valves' position shown on FIG. 48. The solenoid 109 thoroughly displaces the slide valve 107, which firstly displaces the slide valve 106 by means of the action of the point 119, secondly thoroughly compresses the spring 118 on the right of the figure and, finally, places the throat 114 in communication with the pipe 115. As one can see, this allows for evacuation of the fluid contained in the right telescope, whose extreme extension position is ascension of the three inclined planes 86 by the three uneven sections 76 will have caused a displacement axial to the cylindrical ratchet with the result that its disymetrical toothing 72 will be disconnected from the disymetrical toothing 73 of the seat 74. Thus, the angular movement of the joint 4 will be possible in both directions, whilst the snug 79 will exert a sizeable force on the stop 80.

The unblocking of the joint by the axial displacement of the cylindrical ratchet 71 may also be carried out irrespective of the angular stop by an electromagnetic, electromechanical or hydraulic force with the devices described in FIGS. 38 to 40. These devices necessitate the admission of a fluid or electric current supplied by a piloting system to be described later. It is also possible to have an unpiloted entirely mechanical system which, based on the measurement of the bending of the link arm 5 under the effect of the torque, unblocks the joint 4 once the propulsive force exerted by the telescopic devices 3 ceases, i.e. upon termination of the rear stride of the individual.

This mechanical device, which is more complex than the other three, is not described here for reasons of space, but this additional possibility underlines the fact that the devices described do not limit the possibilities of the invention.

FIG. 38 illustrates a first principle for generating an axial displacement of the cylindrical ratchet 71, the latter containing a solenoid 89 which, when traversed by a d.c. current, is displaced to the right around a ferrous core 90 integral with the closing plate 68 of the seat 67. When the current is cut off, the solenoid 89 and the ratchet 71 are brought back to the left by the spring 75 and the toothings 72 and 73 are once again in contact. The electric current is supplied by a wire 91 which arrives via a hole 92 of the end plate of the lower or female part 3i of the telescopic device.

FIG. 39 illustrates a second principle for generating an axial displacement of the cylindrical ratchet 71. An electric d.c. motor 93 is secured via its outer cage to the seat 74. The rotor 94 of the motor is integral with a nut 95 which is able to turn inside the smooth bearings of the outer cage of the motor 93, but which are unable to move axially in relation to it This nut turns around a screw rod 96 which is rotationally immobilized by a pin 97 taking support inside the seat 74. The rotation of the nut 95 thus drives the axial displacement of the screw rod 96 which contains a shaft 98 integral with the cylindrical ratchet 71 and which is constantly thrust back towards the left by a spring 75. When the motor is traversed by a d c. current of a certain direction, the ratchet 71 is thus thoroughly propelled to the right and the toothings 72 and 73 are thrown out of gear. When the motor 93 is traversed by a current opposite to the preceding one, the screw rod 96 is propelled back as far as possible to the left and the ratchet 71 is propelled back to the left solely by the force of its spring 75. The current arrives in the same way as indicated on FIG. 38.

FIG. 40 illustrates a third principle for generating an axial displacement of the cylindrical ratchet 71. A part integral with the ratchet 71 constitutes a piston 98a which can be displaced without a cylinder 99 integral with the seat 74. The displacement towards the left is made with the return spring 75 of the ratchet. The displacement towards the right occurs under the action of a hydraulic thrust, either directly into the volume limited by the cylinder 99 and the head of the piston 98, or by means of a flexible bladder 100 so as to have improved imperviousness. The fluid is admitted via paths similar to those made use of by the electrical wires, and which are described later, at the same time as the means designed to generate the currents or fluid pressures at the times desired.

The force required to carry out the axial displacement of the cylindrical ratchet 71 towards the right is very slight as this displacement only takes place in the absence of any mechanical torque being exerted on the joint 4.

FIGS. 46 to 50 describe the principles for generating and distributing fluids under pressure designed to produce a mechanical extension force inside these telescopic devices 3 which are equipped with an axially extensible sealed chamber.

On these diagrams, the respective scales of the components are not represented so as to be better able to describe the most specific aspects to be applied to the invention in question. These aspects do not, however, limit the possibilities of the invention.

As regards the other aspects, the two overall systems described involve the use of a displacement compressor and a thermal engine controlled by a regulator which automatically controls the required power at the mean pressure which the operator desires to have inside a buffer reservoir. A small electric generator is connected to the thermal engine. The technician is familiar with all these elements which do not limit the possibilities of the invention and shall not be described here, although they concern dispositions which are particularly favorable for the use of the invention in question. Firstly and for reasons of lightness, it is desirable that the largest part of the resistant structure of the motor and compressor be merged and that roddings be avoided, by virtue of the free pistons, or reduced to a minimum. The cooling and thermal insulation systems shall also be common. Finally, the Stirling cycle external combustion engines, for example, will however be slightly heavier, much preferable to internal combustion engines which are far noisier.

Figure 50:
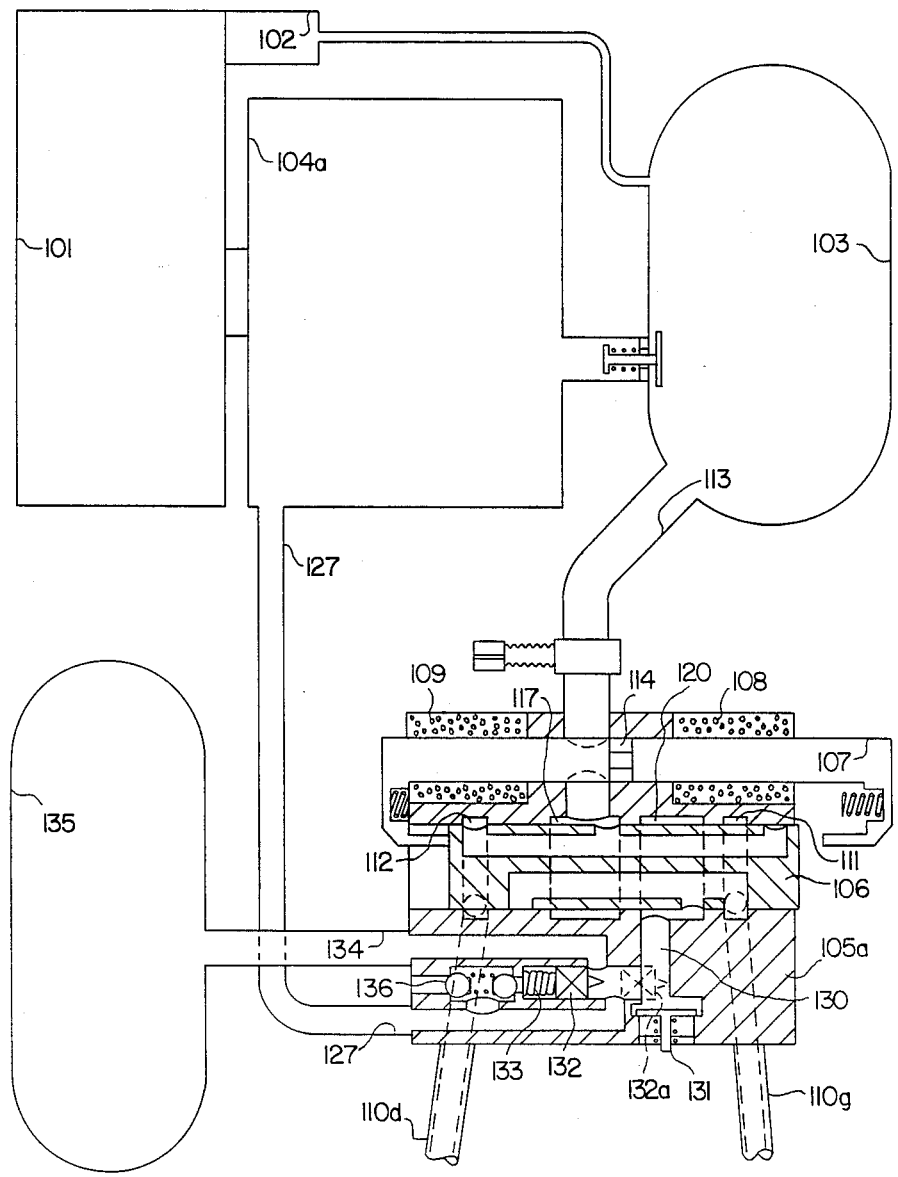
FIG. 50: Diagrammatic overall view of a compressed air generator comprising the engine, compressor, tanks and main piston slide valves of the telescopic devices.

The system described on FIGS. 46 to 49 uses a liquid such as a transfer fluid and the system of FIG. 50 uses a gas which, a priori, is air. The invention's possibilities are not restricted to the use of any particular gas or fluid and possibly include a combustion gas.

FIG. 46 shows the engine 101, the regulator 102 automatically controlling the pressure of the buffer reservoir or tank 103, and the displacement compressor 104.

The driving power varies significantly according to the uses preferentially envisaged for the device, but it occurs mainly within the range of 1 to 10 KW, the majority of applications requiring 2 to 5 KW. For these outputs and purely by way of information, a high-performance motorcompressor set, together with the tanks and distributor, will weigh about from 4 to 8 kg, excluding fuel, which is the weight order of magnitude of manual forest chain saws. In the case of the invention, this weight, secured to the body, is very easy to carry.

The order of magnitude of the maximum output pressures of the compressor is generally within the range of 5 to 50 bars, depending on the section of thrustors used and the type of use sought-after, which normally necessitates the use of a displacement type compressor. These pressures do not pose any problems as regards using flexible pipes, the technician being fully acquainted with the nature of these and thus no description of such nature is required here, and the machining precisions required for the control slide valves have an up-to-date hydraulic equipment value. There also exists a distributor 105 comprising two slide valves 106 and 107. This distribution system common to the left and right telescopic devices 3 has been chosen in this description because it enables all the fluid movements inside the device whilst it is functioning to be compactly represented. But in practice, it is preferable to separate the valves or feed and outlet slide valves relating to each of the telescopic devices 3 as this enables the strong passage sections required to be more easily obtained so as to have slight load losses. The piloting system always remains close to the position indicated on FIG. 55. This distributor 105, represented diagrammatically, is in turn operated in one direction and then the other by the solenoids 108 and 109 respectively. The pipes 110g and 110d connect the distributor to the ductile sealed chamber contained inside the left and right telescopic devices respectively. They come to an end at the grooves 111 and 112 able to communicate with the slide valve 106.

The pipe 113 connects the buffer tank 103 to the wall of the cylinder in which the slide valve slides. This valve has a groove or throat 114 which, when it occupies its extreme axial positions, can be placed in contact with the pipes 115 joined together and, when it occupies its two intermediate axial positions, in relation with the pipe 113. In all the cases, the groove or throat 114 is connected via the passage 116 to the throat 116 able to communicate with the slide valve 106. reached, and its dispatch via the pipe 110d, throat 120, slide valve 106 and pipe 121 into the reservoir 122 At the same time the liquid of the reservoir 122 is sent via the pipe 123, valve 124, pipe 115, throat 114, passage 116, throat 117, slide valve 106 and pipe 110g into the left telescope, the volume of which increases since it extends as shown on FIG. 17.

FIG. 49 is the last of the possible positions of the slide valves following cutoff of the current in the solenoid 109 it corresponds to FIG. 47, inverting the positions of the left and right telescopes. FIG. 18, which corresponds to the start of the weight of the body being applied onto the right leg, is the moment when the distributor passes, owing to cutoff of the electric current, from the position shown on FIG. 46 to that shown on FIG. 47. The only change is the spring-back of the spring 118 situated to the left of the slide valve 107 shown on the figure, which places the throat 114 of this slide valve in communication with the pipe 113 and closes the pipe 120. Thus, the telescopic device of the right leg is fed by the liquid under pressure of the buffer reservoir. At the same time, the position of the slide valve 106 has not moved in relation to the position of FIG. 46 and accordingly the evacuation of the liquid contained in the telescopic device 3g of the left leg can be continued in the direction of the reservoir 122.

FIG. 19 corresponds to the position of the distributor to be seen on FIG. 47.

At the end of the movement shown on FIG. 20, i.e the maximum extension of the right leg, the position of the distributor becomes that shown on FIG. 48. At this moment, the left foot is already in contact with the ground, but it does not yet support the weight of the body. A moment later, the weight of the body rests on the left foot in a position identical to that described on FIG. 18 for the right foot and, at this moment, the distributor takes up the position described on FIG. 49, which admits the actuating pressure in the telescopic device 3g of the left leg. Thus, it can be seen that the system described on FIGS. 46 to 49 ensures power distribution: firstly, according to the pressure variation law desired, thanks to the buffer reservoir 103 and its perfect air or gas supplements 128 or gas supplement approximating the gas-liquid equilibrium 129. Secondly, by cushioning the landing on the front foot, by storing the energy and by checking the maximum flow pumping period of the compressor 104 by virtue of the reservoir 122 containing a perfect gas or air reservoir 126. Finally, by being applied to all the possible displacement cycles which extend from movement comprising leaps to the ascent of slopes, during which the maximum bending of the front leg is attained the moment it alights on the ground. Moreover, the hydraulic circuit can be adapted to many specific applications. For example, a special item of equipment can be provided which enables certain disabled persons to descend steep slopes or stairs without retained muscular efforts in the legs. On the pipes 110 for example, it is merely necessary to provide a valve enabling the telescopes to be quickly filled and evacuated via a very small section which can be adjusted at will.

FIG. 50 illustrates a principle for generating, distributing and recovering compressed air. If the gas used is air, the small leakages are not significant, which enables less expensive equipment to be used. On the other hand, the compressed air or any other gas leaves, in the sealed volume of the telescope in its maximum extension position and prior to evacuation enabling the foot in question to be raised again, a considerable amount of springback energy. This problem does not arise if the fluid is incompressible. It is therefore a distinct advantage to recuperate the greater part of this energy if one wishes to retain sound efficiency of the device. The presence of the unblockable joint 4, which enables the foot to be raised instantaneously, even if the telescopic device remains momentarily extended to the maximum, suffices to to recuperate the spring-back energy of the air if it is drawn back directly int the compressor. However, in certain usages, it may be advantageous to reduce the time involved in evacuating the telescopic device, which results in an intermediate spring-back reservoir being used. Moreover, it is virtually impossible to cushion the fall onto the front foot by means of the air contained in the device once it has been filled with atmospheric pressure. The cushioning of the front fall will be obtained by carrying out a premature admission of compressed air, for example in the position indicated by FIG. 13, by means of the piloting system as shall be seen subsequently.

The system described on FIG. 50 includes, together with the one on FIG. 46, a motor 101, regulator 102 and a displacement compressor 104a sending the compressed air into a buffer reservoir 103 capable of being equipped with a gas reservoir at gas-liquid equilibrium separated by a flexible diaphragm 129 (not represented).

The distributor 105a is equipped with two sliding valves 106 and 107 similar to those of the distributor 105 and functioning in the same way. This distributor 105 has been described by analogy with the system of FIG. 46, but in practice more efficient passage sections can be obtained by separating the right distribution from the left distribution by means of a 3-way electrovalve for each telescopic device connected to the pipe 110g or 110d and in turn to the pipe 113 or 130. The distributor 106 is in communication with the right and left telescopic devices via the pipes 110g and 110d respectively ending at the throats 111 and 112 situated around it.

The throat 117 is also reserved for the supply when in communication with the buffer reservoir 103 via the pipe 113 and the throat 120 is reserved for evacuation/recuperation.

With the pipes 115 suppressed inside the distributor 115a, the throat 114 of the slide valve 107 is not in communication with any orifice when this slide valve occupies its two extreme positions and is in communication with the pipe 113 when it occupies its two intermediate positions. FIG. 50 which, as regards the disposition of the slide valves in communication with the position of the legs, corresponds to FIG. 46 or FIG. 48 by inverting the designation of each leg, more specifically represents the recuperation evacuation of the telescopic device 3g of the left leg. At the moment the slide valve 107, under the effect of the electromagnet 108, arrives to displace the slide valve 106, evacuation begins and air, compressed at high pressure, arrives at the distributor 105a through the pipe 110g. This air is admitted by the slide valve 106 into the throat 120 and the evacuation pipe 130. Its high pressure immediately closes the valve 131 by compressing its spring and thoroughly pushes back the piston 132 by compressing its spring 133. The initial position 132a of this piston is represented in the form of dots. The backward movement of the piston 132 has freed the inlet of the pipe 134 which drives the compressed air towards the intermediate expansion reservoir 135. At the same time, an air flow is admitted into the pipe 127 moving towards the admission or intake of the compressor. This double exit of air thus allows for the quick evacuation of the telescopic device to begin with the result that the compressed air pressure drops instantly. As a result, the piston 132 propelled by the spring 133 re-advances and closes the pipe 134 by imprisoning the compressed air of the intermediate expansion reservoir 135, but still permits pumping by the compressor into the pipe 127, which causes the compressed air originating from the pipe 110g to fall even further. As a result, the valve 131 opens and the piston 132 returns to its initial position 132a. It then causes the compressed air of the reservoir 135 to come into contact with the suction of the compressor which quickly evacuates it. When the reservoir 135 is empty, the suction complement of the compressor is effected by the valve 136. The system described thus enables the telescopic device in question to be emptied very quickly by recuperating, following losses and intermediate expansions, about two thirds of the air expansion energy. However, as indicated earlier, this system or another system having the same objective is not usually necessary, but it is obligatory for applications where the device is required to evacuate the telescopic devices very rapidly. Except for these cases, the evacuation pipe 130 is simply connected to the admission pipe 127 in the compressor and the effectiveness of recuperation is thus improved.

In the system described on FIG. 50, no pipe is provided for the filling of air at atmospheric pressure when the right leg descends. In fact, this filling is accomplished more effectively by a valve (not represented) situated at the top of the telescopic devices under the saddle. The air thus drawn in and then compressed during the descent of the front right foot moreover plays a minor part in the cushioning, but this cushioning remains based mainly on a premature admission of compressed air desired by the individual concerned.

We now come to a description of the complete piloting system of the device and its various partial functions. The skeleton diagrams are shown on FIGS. 51 to 55, but the explanations also need to be related to other figures. Moreover, it needs to be understood that the systems described are double systems: one concerns the left part of the device with possible interactions on the right part and vice versa. The systems selected are amongst the simplest possible applicable to a given device required to function for a wide variety of uses. Of course, it is possible to specialize the piloting systems with a view to using the device in highly specialized preferential ways, some of which will be described in the paragraph relating to the variants of the invention. The device may include:

either a piloting system which is entirely automatic during operation, certain options relating to it possibly being able to be selected prior to start up, or an automatic piloting with manual correction of adjustments during operation, or a piloting which is at least partly manual during operation and reserved for slow rhythm usages.

For all cases, adjustments may be carried out on stoppage so as to favor the use of the device in a certain type of passage. These include, for example, the adjustment of the stop screw 85 of the joint 4 or the adjustment of the electric stop screw 164 situated on the control of the slide valve 107 of the distributor, or the gaseous pressures situated behind the flexible diaphragms 128 and 129 of the buffer reservoirs 103 or storage/recuperation reservoir 125.

The elements or functions of the device which need to be piloted are, at the minimum, the unblocking of the joint 4, authorization for reblocking the joint 4, the filling and evacuation of the sealed and expansible volumes of the telescopic devices 3 if the device includes them, and the pressure of the buffer reservoir 103 automatically controlling the speed of the motor, if the device comprises one. The complete piloting system comprises:

physical data sensors
 a system for processing this data
 devices for mechanically executing orders received by the system
 a system of commands accessible to the individual and accessories which connect him to the data processing system or which act directly on the nature of physical data
 junction wires or tubes between all the preceding elements.

The first of the sensors is the one which detects the maximum extension stop arrival of the telescopic systems.

FIG. 32 shows such a sensor 137 which establishes an electric contact as soon as the piston 49 propelled by the prestressed spring 48 arrives at the end of movement. In this case, the sensor 137 is pressed against the castor or small wheel 45. This representation is diagrammatic and in no way limitative as numerous other dispositions are possible. The sensor 137 could also be secured, for example, to the upper part 3s of the telescopic device and to detect a mechanical or other discontinuity integral with the lower part 3i of this device, etc. It should be noted that the sensor 137 or assimilated device is not represented on FIGS. 29 and 33 solely to simplify the drawing.

Moreover, firstly, the sensor 137 or assimilated device may possibly detect an extension position of the telescopic device 3 which does not correspond to the maximum extension position, but which is chronologically situated slightly ahead Secondly, the sensor 137 may be replaced by a system for continuously detecting the extension position of the telescopic device 3. Such a system can be easily housed, for example, in the cavity existing inside the interior of the pistons 55 and 36, as can be observed on FIGS. 33 and 29. It may consist, for example, of a telescopic device equipped with magnetic signals disposed axially or measuring an electrical resistance proportional to the extension. The taking into account of the indications supplied by this system of detection of the extension position, in the same respect as those of a stop sensor 137, enable the functioning of the device for certain uses to become more flexible.

In effect the length of the mechanically assisted part of the foot extension is defined by the adjustment of the stop 80 with the screw 85, possibly motorizable, but detecting the telescopic extension is another way of adjusting the length of the motor part of the extension and progressively extending the stride once it begins in this case, all that is required is adaptation of the piloting circuits described on FIGS. 52 to 55.

The standard sensor 137 or similar device may firstly trigger an electric signal, as shown o the diagrams of FIGS. 53 to 55, or a hydraulic signal as shown on FIG. 52, which in both cases orders the unblocking of the joint 4 at the end of the propulsive stride so as to enable the foot to be raised.

Secondly, and solely if it triggers an electric signal, it can serve to both order the unblocking of the joint 4 and the evacuation of the fluid contained in the telescopic device 3 if the moving force derives from a compressed fluid. However, it may be desirable that these two functions be chronologically slightly offset and this accordingly necessitates the use of two sensors 137. One of them will detect, for example, the maximum extension stoppage and the other will detect an extension position close to the latter. This chronological possible offsetting of the orders given can also be obtained with a single sensor completed, for example, by an electronic delay.

The second system of detection consists of one or more sensors 138 moving over one or more tracks 139 composed of one or more circular ring fractions centered on the axis of the joint 11 of the saddle and secured, for example, to the middle partition of the latter. This second system can be seen on FIGS. 21 to 28 and 51 to 55. The sensors 138 can also move radially over the track 139.

The representation of the parts 138 and 139 appearing, for example, on FIG. 22 is greatly simplified. Indeed, firstly, the track is a single track although it may comprise several concentric tracks, secondly it does not indicate any thickness variation and finally, the angular position adjustment system is not represented, the reason for this being that FIGS. 21 to 28 relate to general applications which also include the most rudimentary versions.

The role of this second system of detection is to enable certain piloting commands to be synchronized with a particular angular position of the telescopic devices 3 with the saddle or between them such as for example the crossing of the legs represented on FIG. 15, i.e with the extreme angular displacement of the legs the amplitude of this movement varying according to the desire of the user.

In order to detect a particular angular position of the telescopic devices 3 in relation to the saddle or between them, it is possible to use a thickness difference on a certain portion of the circumferential length concerned on the track 139 and visible on FIGS. 52, 53 and 55 where this track appears in profile and shows its variable thickness and its circumferential length. Thus, the small wheel or sliding contact of the sensor 138 only affects the track in the high thickness zone of the latter.

A geometrically uneven section can also be placed on the track 139, as shown on FIG. 54, so that a signal can be recorded by the sensor 138 when it passes above.

In order to obtain the angular position variation of the mark or thickness discontinuity of the track 139, a circular cannelure can be used which is centered on the axis of the joint 11 in which the track 139 is displaced under the effect, visible on FIG. 55, of a rod 140 connected to a screw 141 axially movable by a nut 142 integral with the rotor of an electric step motor 143 controlled by a piloting lever 144. It is obvious that the level differences or uneven sections previously described for the track 139 can be replaced by a magnetic signalling secured to the latter and cooperating with a suitable sensor 138, the technician being thoroughly familiar with such systems. In order to detect the extreme angular displacement of a leg, it is essential to detect the circulation direction change point of the sensor 138 on the track 139. This can be achieved using a sensor 138b of the type described by FIG. 55. This sensor 138b has a sliding contact 145 which comprises an anchoring extremity 146 which, cooperating with a suitable housing, integral with the body of the sensor 138b, enables it to turn slightly inside the plane of the figure and move vertically towards the bottom where it leaves the thickest part of the track 139. The sliding contact 145 is not, however, able to rub over the thinnest part of the track 139. The sliding contact 145 is propelled by an oblique spring 147 which, taking support on the body of the sensor 138b, exerts on it a force towards the bottom and left of FIG. 55. Thus, if the sensor 138b moves towards the left of FIG. 55, a vertical supporting force on the track 139 is given to the sliding contact 145 by the oblique spring 147 as soon as the latter ascends the thick part of the track 139. But the tangential friction force resulting from this during the displacement tends to distance the sliding contact 145 from its left stop 148, which has the effect of further compressing the spring 147 in this position, the sliding contact 145 comes to rest on the electric conductor 149 which establishes contact with the flexible cord 150 welded onto the sliding contact 145 in the only conductive zone of the latter. If the whole sensor 138b now is displaced to the right of FIG. 55, this corresponds to a change of direction of the angular displacement of the leg and telescopic device connected to it. In this case, the tangential friction force on the track 139 tends to cause the sliding contact 145 to come into contact with its stop 148 and to cut off the electrical contact. The other functions of the sensor 138b of FIG. 55 will be examined subsequently.

There also exist other means for detecting the maximum angular displacement of the sensor 138b on the track 139. For example, this unit can be transformed into an electric rheostat comprising an isolated sliding contact and a track 139 electrically insulated from the center partition 19 of the saddle 1, then playing the role of a rheostat it is then easy to continuously electrically determine the value of the mathematical derivative of a current flowing through the system. The nil derivative then corresponds to the change of direction point. This rheostatic system also enables the geometric discontinuities on the track 139 to be suppressed since all that is required is that they be replaced by a measurement of the electrical resistance of the circuit. This also simplifies piloting as it is possible to avoid displacing the track 139 so as to modify the angular position of the mark. For the new critical resistance of the rheostatic system, it is sufficient for the operator to display a value of his choice. The general implantation of the sensors and detectors 137 and 138 is shown on FIG. 51.

First of all, it can be seen that there are one or more flexible cord electrical links between the location of the sensor 138 and a battery 151 or current source derived from the possible motor-compressor set. Then there is an electrical or hydraulic link between the location of the sensor 138 and that of the sensor 137. Finally, there exists an electrical or hydraulic link between the sensor 137 and the bottom of the lower part 3i of the telescopic device 3. After leaving the bottom of the lower telescopic device 3i, this link penetrates the fixed seat or base 74 of the joint 4 via the hole 92 giving access to the pipe 91 through which it is connected to the electromagnetic, electromechanical or hydraulic device which commands the axial displacement enabling the cylindrical ratchet 71 to be rendered inoperative.

The link between the sensor 138, sensor 137 and joint 4 can be effected in the following two ways, having regard to the telescopic movement between the parts 3i and 3s.

Firstly, as can be seen on FIGS. 29, 31 and 32, the link leaving the location of the sensor 138 can be a wire or flexible helicoidal tubular pipe 152 disposed inside the upper part 3s of the telescopic device and penetrating the head of the piston integral with the lower part 3i of the telescopic device, connecting the sensor 137 and then descending as far as the base of the lower part 3i via a conduit drilled into the rod of the piston 36r or 49r.

Secondly, as can be seen on FIGS. 33 and 34, the link leaving the location of the sensor 138 may be a wire or flexible tubular pipe 153 descending into a longitudinal groove, not shown on the diagrams, of the upper part 3s of the telescopic device as far as its junction point with the part 53 where this wire leaving its groove is connected to a sensor 137 and then penetrates a hollow cylindrical lower extension 154 of the support part 58 of the return spring 61, passing between the small wheels 50 and 51. Then the wire or flexible pipe 153 takes the shape of a helicoid and descends inside the split tube 57 as far as the bottom of the lower part 3i of the telescopic device. These two methods are not limitative, but the junction procedure selected must always take account of the sliding telescopic movements which, as one can see, is not too difficult.

The types and detecting sensor principles described do not limit the possibilities of the invention in particular, where the invention or its variants are applied to very specific uses, it is possible to envisage additional or replacement signals being employed.

The first function of the elements of the automatic piloting system is to unblock and authorize the reblocking of the joint 4. The unblocking of this joint always takes place towards the end of the propulsive stride of the foot in question and consequently at the end, or almost at the end, of the extension movement of the telescopic device 3. Earlier, it was mentioned that the operator of the device has the possibility of mutually adapting these elements according to the terrain or speed by means of the stop adjustment screw 85 of the joint 4 and of detecting a signal slightly preceding the extension stoppage of the telescopic device 3. The unblocking of the joint occurs at the end of the movement represented on FIG. 16 or FIG. 20.

Reblocking authorization, i.e the ability of the cylindrical ratchet 71 to prevent the arm from ascending after it has descended from any lower angle or at least any angle equal to the angle defined by the stop screw 85, is given the moment the foot is raised which renders the first to alight on the ground the maximum. In practice, this results in this authorization being given at almost the moment when the foot about to alight on the ground extends in front of the foot already on the ground, i.e. In approximately the position shown on FIGS. 15 and 19.

In order to perform these two functions for unblocking and authorizing the reblocking of the joint 4, the following electrical or hydraulic circuits are used:

If the means for exerting an extension force in the telescopic device 3 is a prestressed and compressed spring 48, the circuits are described on FIGS. 52 and 53.

FIG. 52 shows that the small wheel of the sensor 138 which has acted on a hydraulic piston or flexible bladder can be displaced when the foot is in front of the body in relation to the direction of the movement on the thinnest part of the track 139 and, when the foot is behind the body, on the thickest part of the track 139 When the leg is in the position shown on FIGS. 16 and 20, the amount of liquid contained inside the sensor 138a is thus minimal if at this moment, the stop sensor 137 comes to a stop, its hydraulic piston or flexible bladder ejects a quantity of liquid which can then only enter the cavity 100 and propel the piston 98a in the cylinder 99. This provokes the unblocking of the joint 4, as can be seen on FIG. 40. With prestressing of the spring 48 being exerted continuously, the joint 4 remains unblocked throughout the ascent of the foot in question. But, when this foot extends beyond the one then on the ground in the configuration appearing on FIGS. 15 and 19, by inverting the left and right foot on these figures, the small wheel of the sensor 138a falls onto the thinnest part of the track 139. This frees a volume which can be occupied by the liquid and, under the effect of the spring of the ratchet 75, enables the cylinder 99 to be evacuated and the piston 98a to move backwards. Thus, the ratchet 71 is again ready to operate. When the joint 4 is blocked following the alighting of the front foot, a compression force is exerted on the spring 48, which suppresses the compression force on the sensor 137, and makes available inside the latter a space which the fluid inside the sensor 138a will occupy when the sensor ascends the thick part of the track 139 and so on. FIG. 53 shows an electrical system with a battery, the principle of this system being identical to that of the hydraulic system. When the stop sensor 137 establishes a contact on the circuit, the contact of the sensor 138a is established since the small wheel is on the thick part of the track 139 and accordingly the electromagnet 89 taking support on the core 90 unblocks the joint 4, as can be seen on FIG. 38. The action of this electromagnet is suppressed by breaking of the contact 138a following the crossing of the feet which re-establishes the initial role of the ratchet 71.

If the means for exerting an extension force inside the telescopic device 3 is a fluid pressure, the circuit is described on FIG. 54 which refers to FIG. 39 as regards the mechanical unblocking means, namely an electric motor 93 acting on an axial nut 95 and axial screw 96. In this case, the control mechanism consists of sending a d.c. current of a first direction into the motor so as to unblock the joint 4, and a d.c current of the opposite direction so as to obtain authorization of the reblocking of the joint.

The track 139 has only one uneven section corresponding to the position of the small wheel of the sensor 138a at the moment the rear foot is raised and extends beyond the foot on the ground.

FIG. 54 shows that when the sensor 137 detects the stop position following the extreme extension of the telescopic device 3, it establishes a double electrical contact in 155 and 156 which sends a d.c current of a first direction into the motor 93 and unblocks the joint 4. If the force stops on the sensor 137 before the maximum ascent of the foot in question because the fluid pressure has fallen too quickly, nothing changes in the position of the ratchet since the motor 93, nut 95 and screw 96 have placed it an irreversible unblocked axial position. When one of the feet of the individual extends in front of the other, the uneven section of the track 139 establishes a double contact 157 and 158 which sends into the motor a d.c. current pulse of the opposite direction to that which has been sent to it by the sensor 137 and accordingly, the joint 4 is replaced in the possible blockage position. In this case, it is also possible to use the mechanical unblocking means described on FIG. 38, provided the command circuit of FIG. 53 is supplemented by an electromagnetic relay of the type which will be described for FIG. 55 and which enables the contact established by the sensor 137 to be maintained in the absence of propelled force until the contact is cut inside the sensor 138a.

The second function of the elements of the automatic piloting system is to evacuate and supply with fluid the ductile sealed volumes contained inside the telescopic devices 3.

As regards the most routine applications of the device according to the invention, evacuation of the telescopic devices commences at the end of the propulsive stride made by the individual, thus corresponding to the end of the operation described on FIGS. 16 and 20 and therefore close to the maximum expansion of the telescopic devices 3.

In the majority of cases, the detection of this maximum extension position by the sensor 137 will have a dual purpose, firstly for evacuating the telescopic devices 3 and secondly for unblocking the joint 4, although the circuits relating to these operations have been distinguished so as to favor the explanation. There are, however, cases where it might be necessary to have two sensors 137, one of which will detect a signal slightly prior to the maximum extension position of the telescopic device. The automatic supply of fluid under pressure to the telescopic devices greatly depends, contrary to evacuation, on the way the device is used. Earlier, it was stated that the supply is carried out by the distributor 105 or 105a by means of two slide valves 106 and 107, the functioning of which has already been explained: the displacement of the slide valve 106 is obtained by the current being sent into one of the solenoids 108 or 109 which provokes the maximum axial displacement of the slide valve 107 which drives the slide valve 106 and places it in the evacuation position of one of the telescopic devices. Admission may only take place into the other telescopic device when the current in the electromagnet in question is disconnected.

Consequently, if a sensor 137 belonging, for example, to the right side of the device according to the invention, makes contact in the electromagnet 108 in order to evacuate the right telescope, it is the sensor 138b of the right side and track 139 of the right side upon which cutoff of the current in the electromagnet will depend, including the admission of fluid into the left telescope.

The individual using the device can move as indicated by FIGS. 12 to 17, i e according to a more or less accentuated mode of leaping effected on a flat or inclined surface. He can also move as indicated by FIGS. 18 to 20, i.e. in such a way that after the foot has touched the ground in front, there is a need for the instant or almost instant supply of the telescopic device connected to this foot. The cutoff of the current in the electromagnet 108 will not, in these two cases of application, be due to the same physical parameter. In the first case, the cutoff will be due to the passage of the sliding contact 145 of the sensor 138b over a thickness discontinuity of the track 139 and in the second case, cutoff will be due to inversion of the rubbing direction of the sliding contact 145 over the track 139.

These, however, are extreme cases and numerous intermediate cases are possible which each time may include: a manual intervention upon stoppage prior to start up concerning adjustment of the automatic piloting; continuous manual intervention during the movement of the automatic piloting adjustment; and finally a fully manual piloting.

The operational diagram of FIG. 55 takes into account all these intermediate eventualities and the extreme cases. In order to establish the current inside the feed circuit of the solenoid 108 activating the slide valve 107, the following conditions are necessary:

There is a d.c. current sent by the source 151

The manual contact is established

The sensor 137 is in the end of movement stop position and its contact is established The contact takes place inside the sensor 138b.

Accordingly, the current passes into the solenoid 108 and into the relay electromagnet 161 which is displaced axially and makes contact in 162 and 163. In this way, if the mechanical contact ceases on the sensor 137 and the current is cut off, nothing will be changed following the operations. The current will then pass into the whole of the circuit until the moment it is cut off by the sensor 138b, which will trigger the admission of fluid into the other telescope, the solenoid 108 no longer being supplied.

If the individual moves according to a leaping mode, the adjustment screw 164 is unscrewed to the maximum towards the bottom so that the placing of the sliding contact 145 on the stop 148 cannot cut the current, as the flexible conducting blade 149 is able to descend onto its inclined contact and support plane. Thus, it is essential to wait until the sliding contact 145, coming from the left of the figure, i.e. from the extreme rear position of the telescopic device in the course of being emptied following establishment of the current, reaches the discontinuity of the track 139 and is above the thinnest part of the latter in order that the current be disconnected. With the manual correction means of the automatic piloting device consisting of a handle 144 sending, along with a separate electrical circuit, pulses to the step motor 143, the individual has the means to displace the discontinuity position of the track 139. Consequently, if he moves the track towards the left of the figure, the current will each time be automatically cut off sooner, which will favor, for example, the ascent of a slope in the leaping mode.

If the individual moves slowly up a steep slope or staircase, there is an immediate or almost immediate need to supply the telescopic device connected to the foot which has just touched the ground. Prior to starting, the adjustment screw 164 is rescrewed towards the top so as to prevent the conductive flexible blade 149 from descending too low onto its inclined contact support plane. Thus, when the sensor 138b, which was moving towards the left of the figure whilst keeping its sliding contact in contact with the blade 149, reverses its movement and moves towards the right, the contact is cut instantly or almost instantly according to the path length on the inclined plane which the adjustment of the screw 164 will authorize to the blade 149. The individual can also climb stairs or very steep slopes without this latter system and by using the preceding device with a suitable adjustment of the discontinuity position of the track 139, provided he moves at a certain speed, and with a more clearly defined scissor movement of the legs. The second device is merely intended to increase precision in certain cases, generally involving less frequent uses. Moreover, the adjustment movements made by the screw 164 are described here in a very simplified way and they may be motorized so as to allow for continuous manual interventions as regards the automatic piloting.

Finally; there is one last piloting mode which is fully manual. The screw 164 is again adjusted towards the bottom prior to starting so that only the thickness difference of the track 139 can disconnect the current. Whilst moving, with each step a premature manual disconnection is effected on the circuit by means of the manual contactor 160. This piloting mode applies to very slow movements, for example to movements made by disabled persons climbing a staircase.

The last essential function to be piloted will only be described briefly as it is not characteristic of the invention and the technician is well-acquainted with the means of embodiment. The individual who uses the device according to the invention must naturally be conversant with the driving power. The parameter which basically concerns him is solely the mean pressure present in the buffer reservoir 103. It is upon this pressure that the relative strength of the extension force of the telescopic devices depends and accordingly the effectiveness of the leg-propulsion assistance movement.

This parameter operates independently of the other piloting aspects of the device, thanks to a manual control disposed on the same handle as that of the contactor 160 and automatic admission adjustment control 144. This handle, turning in two directions and/or fitted with pushbuttons depending on the case, can be simply held in the hand and connected to the device by a bundle of flexible cords. It may also be integral with the device like the support handles 180 as shall be seen subsequently. This control, which displays the individual's desire for a more or less high pressure in the buffer reservoir 103, acts directly on the regulator 102 which automatically controls the power of the motor at the mean pressure selected for the reservoir 103, irrespective of the flowrate required and within the limits possible, by the telescopic devices 3. The use of the device does not constitute any danger to the individual since he can progressively increase the pressure of the reservoir 103 according to the requirements and possibilities of a given distance and having regard to his physical capabilities. FIGS. 57 to 62 relate to several variants of the device according to the invention.

FIGS. 56 and 57 describe a mechanical system for assisting the scissors movement of the legs, i.e. via a pendulum movement of the telescopic devices 3. This system uses the whole of the device according to the invention and thus constitutes a simple addition to the latter without requiring any modification of the dispositions previously described. The top of each telescopic device 3 is connected via a joint 167 to a telescopic jack 166, an opposite joint 168 of which is connected to a fixed point sufficiently integral with the saddle and situated behind the latter. For example, on FIG. 56, the joint 168 is secured to the base of the engine unit 7, but this is not limitative. The jacks 166 have pistons 169, the travel of which is sufficient so as not to impede the complete pendulum movements of each of the telescopic devices 3. The supply of the jacks 166 with compressed fluid is very simple as each of them is connected to the feed pipe of the left or right telescopic device opposite it in relation to the center partition of the saddle. This thus enables the leg in the air to be projected towards the front, whilst the leg on the ground and behind effects the propulsion. However, the evacuation of these jacks 166 can only be effected in certain uses not involving leaping and is also effected much more rapidly than evacuation of the telescopic devices 3 as these benefit from the part played by the unblockable joints 4. Consequently, the pipes 169 which connect each jack 166 to the feed pipe of the opposite telescopic device 3 are fitted with a three-way electrovalve 170 which enables either the jacks 166 to be fed or the feed pipe 169 to be disconnected and the jack to be placed in communication with a pipe 171. This pipe 171 is connected to the atmosphere if the propulsion fluid is compressed air and connected to a valve 172 situated at the input of the other jack 166 if the propulsion fluid is a liquid. Thus, the resistant mechanical force exerted by the jacks 166 whilst they are being emptied is negligible. The electrovalves 170 are controlled by means of a contact established by the sensor 137 previously described. It is desirable that, when the device according to the invention is fitted with the jacks 166. it also includes the three conical gear wheels 25d, 25g and 26 which maintain the angular position of the saddle 1. However, if the jacks 166 are dual-effect jacks, the face 174 of the pistons 173 can exert pressure on a liquid which causes the pipe 175 to communicate the two jacks 166. Thus, the advance of one of the pistons 173 must be accompanied by an identical backward movement of the other piston 173, which provides a certain degree of angular stabilization between the saddle and the bisectrix of the angle formed at any moment by the two telescopic devices 3.

FIGS. 58 and 59 describe a profile and back view of the device according to the invention equipping an individual. In this case, the device possesses two types of support to be added to the body, these two elements able to be employed independently of each other.

The normal support transmitting the ascending forces produced by the device is the saddle 1. These forces thus concern the base of the individual's spinal column. The means described on FIGS. 58 and 59 are intended to also concern the top of the spinal column by means of an ascending action exerted either on the hands or under the shoulders or on both places at the same time. For a normal person, the advantage is that it is possible to distribute the forces received in several points instead of one point, which can increase comfort, especially if the power of the device is high and, for a disabled person, can reduce a deficiency of the spinal column. Moreover, the fact of using a shoulder support connected by a rigid bar to the saddle 1 enables, if required for certain usages, additional degrees of stabilization to be given to the saddle in relation to the body. The suspension under the shoulders includes a means of support 176 which may be a sectional metal or plastic bar, more or less flattened, in order to be fully adapted to the shape of the back and be terminated by concave parts towards the top passing under the shoulders. The part 176 could also end above the shoulders and support the latter by means of belts passing below the arms or any other suitable means. The unit may also be supplemented by a belt passing in front of the chest so as to increase stability. Generally in its middle, the part 176 has a joint 177 whose axis is roughly parallel to the ground and longitudinal in relation to the body. This joint can be blocked for certain usages.

A sectional plastic or metal link bar 178, extensively flattened and enlarged so as to better adapt itself to the back, descends against the latter until it reaches a joint 179 secured to the rear of the saddle 1. This joint has an axis longitudinal in relation to the saddle and body and roughly parallel to the ground and another axis perpendicular to the center plane of the saddle.

With these two axes, the joint 179 prevents the bar 178 from exerting any torque on the saddle, but, as indicated earlier, it may be advantageous in certain usages of the device for the bar 178 to be able to exert a torque on the saddle so as to keep it in position. Consequently, the two axes of the joint 179 are blockable, simultaneously or separately. The professional concerned is sufficiently familiar with the possible blocking means that they need not be described here.

The suspension by the hands means includes two handles 180 disposed symetrically in relation to the body and some centimetres away from the thighs. The axis of these handles 80 is roughly parallel to the ground when the device is mounted on the individual who is standing and these handles are roughly parallel to each other. They are integrally connected to the rear of the saddle by metal or plastic slightly bent tubes which pass round the back of the individual's thighs, whilst leaving a clear space for them. The slightly bent tubes 181 are secured to the resistant structure of the rear of the saddle by a means which also permits adjustment of the angular position around an axis perpendicular to the center plane of the saddle. This means may consist, for example, of a collar nut which comes and locks against the male threaded part, integral with the saddle, a radial toothing collar on the end of each tube 181. Thus, the individual can adapt the height of the handles to the length of his arms so as to be in the most favorable position upon the transmission by the latter of a sizeable vertical force. If the device includes a motor-compressor set, one or both of the handles can also function as piloting controls like a motorbike.

FIGS. 60 and 61 describe two variants of the telescopic device 3 according to the invention. They solely concern the way to make sliding possible in the presence of a torque, but the other functions of these telescopic devices, i.e. the application of an extension force by a spring or fluid and return springs, are realized by adapting the principles already described and thus will not be repeated here. Moreover, the joints on the saddle and the blockable and unblockable joint 4 are also identical to those of the nominal telescopic device 3 and the means for implementing the piloting.

FIG. 60 shows a rigid metal bar 182 leaving the joints of the saddle and ending at a joint 183 whose axis is roughly perpendicular to the center plane of the body. The joint 183 is connected to a metal plate 184 which bears the blockable and unblockable joint 4 and a joint 185 whose axis is roughly perpendicular to the center plane of the body. The joint 185 is connected to a sliding male or female part of a telescopic jack 186 whose other sliding male or female part is connected via a joint 187, whose axis is roughly perpendicular to the center plane of the body, to the bar 182.

FIG. 61 shows a rigid metal bar 188 leaving the joints of the saddle and ending at a joint 189 whose axis is roughly perpendicular to the center plane of the body. The joint 189 is connected to a metal plate 190 which carries the blockable and unblockable joint 4 and a joint 191 whose axis is roughly perpendicular to the center plane of the body. The joint 191 is connected to the sliding male or female part of a telescopic jack 192 whose other sliding male or female part is connected, via a joint 193 whose axis is roughly perpendicular to the center plane of the body, to the bar 188. Thus, it can be seen that the bars 182 or 188 and the plates 184 or 190 to which they are joined are one way of replacing the small wheels of the telescopic devices 3 previously described and enable the propulsive force to be obtained under the effect of the expansion of the telescopic jack 186 or shortening of the telescopic jack 192 without either of the latter having to undergo a torque These two procedures which bring into play the most significant forces in the jacks require sections as large as for those described so far and relatively cumbersome. On the other hand and although it is possible to fit the nominal telescopic devices 3, equipped with small wheels, with twin-action jacks enabling the foot to descend and be raised by means of a piloted mechancial action, the telescopic jacks 186 or 188 can be more easily adapted to this application intended, for example, for certain disabled persons. For certain of these applications of the device according to the invention requiring twin-action jacks capable of also permitting assistance to be given to the raising of the foot, it is possible to replace the blockable and unblockable joint 4 by a rigid fixing of the link arm 5 onto the telesopic device as the use then generally only includes sufficiently slow movements. It is also possible to block the joint 6 so as to render the shoe integral with the arm 5.

FIG. 62 shows an additional means to enable the foot to rotate around the axis of the legs by means of the device according to the invention. The link arm 5 is fitted with a joint 4 whose axis is roughly perpendicular to the ground and is situated close to the joint 4. This process may enable wider technical choices to be made as regards the telescopic devices 3 with small wheels of FIGS. 29 to 34 if they are no longer required to provide a mutual rotation of the sliding parts around their longitudinal axis. In particular, it is applicable, just as any other process is applied and plays the same role and is secured to the base or top of the telescopic devices, in the case where the sliding is not rectilinear or in the case of the telescopic devices of FIGS. 60 and 61. There are a certain number of special energy supply modes and variants of the device when the latter only requires a very short autonomy. The usages for which it is then reserved are preferably the repeated ascent of a steep slope or staircase where the relief variations do not exceed several tens of meters and generally also over a distance of some tens of meters. The applications may concern the work in certain mines or on a building or civil engineering site for example, or even the climbing by disabled persons or physically handicapped persons of stairs in premises in which it is difficult or too expensive to instal any elevator system.

The first solution consists of connecting a very high pressure compressed air reservoir, fitted with a pressure reducing valve, directly to the pipe 113 of FIG. 50. The expansion energy is not then recuperated and evacuation occurs into the open air via the pipe 130. The relief variation autonomy is short and depends on the amount of mechanical propulsive work required from the device compared with the work supplied by the legs. On the other hand, the covered distance autonomy is not restricted.

The second solution consists of feeding the pipe 113 of FIG. 50 by means of a long and fine flexible pipe which continuously provides compressed air deriving from a fixed source. The sources of compressed air are widely used in diverse plants or sites so that it a simple matter for the worker carrying the device and needing to locally carry out arduous uphill work to connect its flexible pipe close by. The relief variation and covered distance autonomy is relatively slight, but the work required may be continued indefinitely. This means can also be advantageously used by disabled persons for climbing stairs as it is easy to make the compressed air flexible pipe descend to the middle of the stairway however small it might be and a priori regardless of the number of floors. Further on in the text, it shall be seen how the device can be quickly positioned on the body for this particular usage. Consequently, the physically disabled person, capable of walking for example, as would be a person suffering from heart disease, but incapable of climbing a staircase, could constantly leave a personal device reserved for this particular use close to the staircase he needs to climb frequently. The third solution consists of providing the device with an electric motor motor-compressor set and to feed this by means of a flexible cord in conditions identical to those cases using a compressed air flexible pipe.

The fourth solution, which calls for the use of electrical energy supplied by a flexible cord or, for a very slight autonomy, supplied by a portable battery, necessitates a technological variant to be applied to the mode for exerting the extension force inside the telescopic devices 3. The explanation, a very simple one, refers to the existing drawings. On FIG. 33, the piston and its lower extension piece 57 is retained. The return spring 61 and its support plate 58 are suppressed. The diameter of the screw 50 is reduced so as to free the center of the split tube 57. A ball circulation nut, with which the professional concerned will be familiar, is secured to the top of the piston 55. A screw rod whose axis merges with that of the upper or male part 3s of the telescopic device is able to rotate inside this ball nut and it traverses the top of the part 3s. This passage is effected by means of a ball bearing which enables it to rotate and exert significant axial forces. After crossing the top of the part 3s, the screw rod is secured to a cylindrical cog wheel forming part of a speed reducer gear with parallel axes, the last of which is integral with an electric motor. The axis of this motor is thus parallel to that of the telescopic device 3s and at such a distance that the outer spatial requirement of the motor just allows for the passage of the female or lower part 3i of the telescopic device when it is sliding. Consequently, the electric motor is only secured via its upper extremity to the speed reducer gear with parallel axes which is itself secured to the upper extremity of the part 3s of the telescopic device. The disposition of this motor, underneath the top of the part 3s, does not increase the vertical spatial requirement of the latter at the thin part close to the parallel axes speed reducer gear. The pendulum movement of the telescopic devices 3 thus remains sufficient. This mode for exerting the extension force of the telescopic devices 3 thus requires the use of a left and right electric motor, but all the devices represented on FIGS. 46 and 50 are suppressed. The motors, screws and ball nuts perform the extension and shortening movements of the telescopic devices. The types of piloting possible are derived directly from those described earlier and represented on FIGS. 51 to 55.

The device according to the invention and provided with the above variant no longer merely applies to relatively slow propulsive movements, but is also suitable for the ascent of stairs by disabled persons or for assistance in certain arduous work undertakings.

For very regular usages of the device according to the invention, such as the ascent of several floors or storeys by means of stairs, it is possible to position the device on the body in a very improvised and quick way: the joints 6 are then secured to the top of rigid cavities with thin sheet metal or plastic walls into which it is possible to insert the end of the shoes which will be slightly wedged inside them owing to an internal foam rubber coating, for example, existing inside such cavities. The device then behaves to some extent as if the joints 6 were rigidly connected to the shoe. Moreover, the saddle 1 does not then possess the hip-fastening device 2. Conversely, it is provided with two lateral handles 180 which are sufficient to keep it in contact with the body for a short while. Thus, the user who is in a hurry need only insert the two tips of his shoes in the cavities connected to the joint 6 and place the saddle under his buttocks, whilst holding the handles, and he can start to move immediately. The cavities connected to the joint 6 do not limit this rapid use of the invention and it is possible to envisage other types of improvised means for hooking the joint to an ordinary shoe.

The device according to the invention can also function, without a motor, as a neutral vertical position seat enabling certain paint works, etc., to be performed. Forces are then transmitted by liquid. A reservoir 103 contains, behind a flexible bladder 129 or system of pistons, a quantity of gas which, as regards the temperature and pressures concerned, exists in conditions approximating its liquid-gas equilibrium. Accordingly, the change in volume of the latter is accompanied by a slight pressure which enables a force relatively constant all along the movement of the telescopic device 3 to be exerted on a piston contained inside the latter and for a seat of neutral height to be provided.

As has been mentioned several times with regard to certain particular aspects, the invention is not limited solely to the forms or means described and represented. Equivalent forms, or different means with which the professional concerned is familiar and whose implementation would not contribute any genuine inventive activity, form part of the invention, the range of which is indicated by the claims which follow.

I claim:

1. A mechanical leg-propulsion assistance device comprising a saddle having means for fastening the saddle to the hips, shoulders or hands of a user, said saddle having a center plane and having attached to said center plane a first joint, said joint having an axis which is about perpendicular to the center plane of the saddle, and to which first joint are connected two telescopic rods with one end of each rod attached to said first joint, one of the rods situated on each of the sides of said center plane, the other end of each of the telescopic rods comprising a second joint whose axis is about perpendicular to the longitudinal axis of each of the telescopic rods, said second joint having an automatic blocking and unblocking device and being connected about perpendicular to the longitudinal axis of a link arm whose other end comprises a third joint having an axis which is about parallel to the axis of said second joint, which third joint connects the link arm to means for securing the link arm to the front of a user's shoes so that the axis the third joint is spaced from and about parallel to the plane of the sole of the shoe, the shape of the link arm enabling it to rotate freely around the third joint without impeding the shoe, the two telescopic rods being fitted with associated motor means which, when the second joint is blocked, can assist the leg propulsion muscular force of a user.

2. A mechanical leg-propulsion assistance device according to claim 1, wherein the first joint of the saddle comprises a connecting member enabling the telescopic rods to be distances laterally in relation to said center plane, the connecting member being rotatably attached to and extending from the saddle and being rotatably attached to the telescopic rods, the connecting member having an angular stop which prevents the telescopic rods from crossing the center plane and thus impeding each other.

3. A mechanical leg-propulsion assistance device according to claim 1, wherein a first conical cog wheel sector integral in rotation with each of the two telescopic rods and centered on the first joint of the saddle, cooperates with a second conical cog wheel rotating freely on a spindle situated in the said center plane and integral with the saddle with the result that, during pendulum movements of the telescopic rods around the first joint, the angle formed by the bisection of the variable angle existing between them with the axis of the second conical cog wheel remains constant.

4. A mechanical leg-propulsion assistance device according to claim 1, wherein the telescopic rods are composed of at least one male element and one female element comprising a cylindrical tubes able to slide into each other, by means of rotatable guidance means between the two elements such that a rotational movement of the guidance means is caused by a relative movement of the male and female elements in the direction of the longitudinal axis of the male and female elements, the male element being connected to a support for the guidance means and which guidance means roll inside a non-circular section of the female element and the telescopic rods possessing a helical return spring which allows the male element to return into the female element.

5. A mechanical leg-propulsion assistance device according to claim 1, comprising exertion means inside the telescopic rods capable of exerting a force to extend them, which exertion means is either a spring compressed at the time of shortening of the said telescopic rods, or a screw disposed and immobilized axially inside the male or female element cooperating with a nut integral with the other element, or a ductile sealed chamber capable of receiving a fluid under pressure and enabling the latter to exert a moving force on the extremities of the chamber, these extremities being integral with the male and female elements respectively.

6. A mechanical leg-propulsion assistance device according to claim 1, comprising external driving power means to expand the telescopic rods, which means is attached both to the saddle and the rods and which exerts a force by the action of an electric motor, a fluid under pressure, either from a motor-compressor or a compressed gas tank, and, where the force is exerted by said external driving power means to a screw and nut means contained inside each telescopic rod and by rotating the screw or the nut by means of a reduction unit.

7. A mechanical leg-propulsion assistance device according to claim 1, wherein the second joint enables the telescopic rod and link arm to expand from a first folded up position to a second position freely opened out as far as the maximum angular opening autherized by stopping means but said second joint does not permit the opposite angular movement due to the presence of a ratchet, the action of the ratchet being suppressed automatically when the expansion of the telescopic rod almost reaches the maximum, this ratchet being automatically activatable to again prevent said opposite angular movement when the telescopic rod starts to extend again, which corresponds to the mutual crossing point of the telescopic rods around the first joint of the saddle.

8. A mechanical leg-propulsion assistance device according to claim 6, wherein the second joint can be permanently blocked and, the external driving means which exerts a force to extend the telescopic rods is also able to exert a force to contrast the rods.

9. A mechanical leg-propulsion assistance device according to claim 1, wherein the telescopic rods each comprise a telescopic jack capable of sliding extension or contraction, the sliding of which in the presence of a torque exerted by the link arm is made possible either by a rigid bar connected to each of the first and second joints and also to one end of the telescopic jack, and there being a connection of the second joint at the other end of the telescopic jack; or by a rigid bar connected to each of the first and second joints and to one end of the telescopic jack; the other end of the telescopic jack being fixed on a point of a plate connected to the second joint, the axes of all the joints being about perpendicular to the plane formed by the jack and the link arm.

10. A mechanical leg-propulsion assistance device according to claim 1, comprising a pair of telescopic jacks wherein at one point close to the end near the saddle, each of the telescopic rods are respectively connected to one end of the telescopic jacks, and wherein the telescopic jacks are connected to a point integral with the saddle and situated behind the latter, the telescopic jacks being symmetrical in relation to the center plane of the saddle and each possessing an internal cylinder forming imperviousness with a piston capable of exerting, under the effect of the pressure of a fluid, a force propelling the telescopic rods toward the front of the device simultaneously with a movement of the user's leg, a pipe connecting the inner cylinder of the jacks so that the thrust towards the front made by a jack on one of the telescopic rods is accompanied by a thrust towards the rear by the other jack onto the other telescopic rod for retaining the mean angular stability of the saddle in relation to the user's legs.

* * * * *